(12) United States Patent
Mammen et al.

(10) Patent No.: US 7,550,595 B2
(45) Date of Patent: Jun. 23, 2009

(54) BIPHENYL COMPOUNDS USEFUL AS MUSCARINIC RECEPTOR ANTAGONISTS

(75) Inventors: Mathai Mammen, Redwood Shores, CA (US); Yu-Hua Ji, Redwood City, CA (US); YongQi Mu, Los Altos, CA (US); Craig Husfeld, Redwood City, CA (US); Li Li, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 11/880,002

(22) Filed: Jul. 19, 2007

(65) Prior Publication Data

US 2007/0292356 A1 Dec. 20, 2007

Related U.S. Application Data

(62) Division of application No. 11/077,433, filed on Mar. 10, 2005, now Pat. No. 7,288,657.

(60) Provisional application No. 60/552,443, filed on Mar. 11, 2004.

(51) Int. Cl.
C07D 221/02 (2006.01)
C07D 405/00 (2006.01)
C07D 211/00 (2006.01)

(52) U.S. Cl. .................. 546/112; 546/214; 546/188

(58) Field of Classification Search ................ 546/112, 546/214, 188

See application file for complete search history.

(56) References Cited

U.S. PATENT DOCUMENTS

| | | | |
|---|---|---|---|
| 6,617,325 B1 | 9/2003 | Lehman-Lintz et al. |
| 6,635,764 B2 | 10/2003 | Mammen et al. |
| 6,656,694 B2 | 12/2003 | Mammen |
| 6,693,202 B1 | 2/2004 | Aggen et al. |
| 2003/0018019 A1 | 1/2003 | Meade et al. |
| 2004/0167167 A1 | 8/2004 | Mammen et al. |
| 2004/0209860 A1 | 10/2004 | Mammen et al. |
| 2004/0209915 A1 | 10/2004 | Mammen et al. |
| 2005/0113417 A1 | 5/2005 | Mammen et al. |
| 2005/0203083 A1 | 9/2005 | Mammen et al. |
| 2005/0203131 A1 | 9/2005 | Mammen et al. |
| 2005/0203132 A1 | 9/2005 | Mammen et al. |
| 2005/0203134 A1 | 9/2005 | Mammen et al. |
| 2005/0203137 A1 | 9/2005 | Mammen et al. |
| 2005/0203138 A1 | 9/2005 | Mammen et al. |
| 2005/0203139 A1 | 9/2005 | Mammen et al. |
| 2006/0205775 A1 | 9/2006 | Ji et al. |
| 2006/0205784 A1 | 9/2006 | Mu et al. |
| 2006/0205946 A1 | 9/2006 | Ji et al. |

FOREIGN PATENT DOCUMENTS

| | | |
|---|---|---|
| EP | 0 747 355 A1 | 12/1996 |
| WO | WO 95/06635 A1 | 3/1995 |

OTHER PUBLICATIONS

Broadley et al., "Muscarinic Receptor Agonists and Antagonists", Molecules, 6, pp. 142-193 (2001).
Eglen et al., "Muscarinic Receptor Subtypes:Pharmacology and Therapeutic Potential", DN&P, 10(8), pp. 462-469 (1997).
Zlotos et al., "Muscarinic receptor agonists and antagonists", Exp. Opin. Ther. Patents, 9(8), pp. 1029-1053 (1999).
Naito et al., "Selective Muscarinic Antagonist. II. [1)] Synthesis and Antimuscarinic Properties of Biphenylylcarbamate Derivatives", Chem. Pharm. Bull., vol. 46, No. 8, pp. 1286-1294 (1998).
Hcaplus 129:58129a, "Selective muscarinic antagonists. II. Synthesis and antimuscarinic properties of biphenylcarbamate derivatives", Naito et al.

*Primary Examiner*—D. Margaret Seaman
*Assistant Examiner*—Nizal S Chandrakumar
(74) *Attorney, Agent, or Firm*—Jeffrey A. Hagenah; Shelley Eberle

(57) ABSTRACT

This invention provides compounds of formula I:

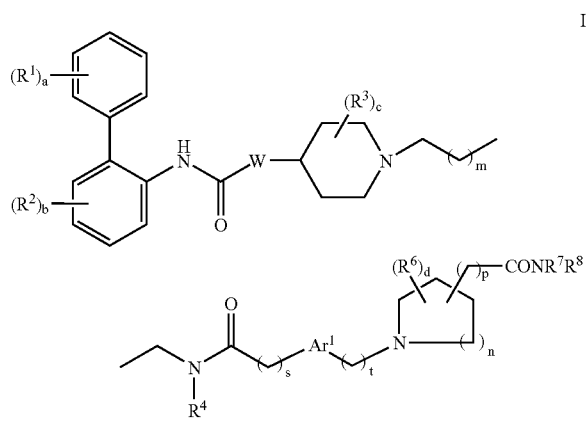

wherein a, b, c, d, m, n, p, s, t, W, $Ar^1$, $R^1$, $R^2$, $R^3$, $R^4$, $R^6$, $R^7$, and $R^8$ are as defined in the specification. The compounds of formula I are muscarinic receptor antagonists. The invention also provides pharmaceutical compositions containing such compounds, processes and intermediates for preparing such compounds and methods of using such compounds to treat pulmonary disorders.

22 Claims, No Drawings

BIPHENYL COMPOUNDS USEFUL AS MUSCARINIC RECEPTOR ANTAGONISTS

CROSS-REFERENCE TO RELATED APPLICATIONS

This application is a divisional application of U.S. Ser. No. 11/077,433, filed Mar. 10, 2005, now U.S. Pat. No. 7,288,657 which claims the benefit of U.S. Provisional Application No. 60/552,443, filed on Mar. 11, 2004; the entire disclosures of which are incorporated herein by reference in their entirety.

BACKGROUND OF THE INVENTION

1. Field of the Invention

The present invention relates to novel biphenyl compounds having muscarinic receptor antagonist or anticholinergic activity. This invention also relates to pharmaceutical compositions comprising such biphenyl compounds, processes and intermediates for preparing such biphenyl compounds and methods of using such biphenyl compounds to treat pulmonary disorders.

2. State of the Art

Pulmonary or respiratory disorders, such as chronic obstructive pulmonary disease (COPD) and asthma, afflict many millions of people worldwide and such disorders are a leading cause of morbidity and mortality.

Muscarinic receptor antagonists are known to provide bronchoprotective effects and therefore, such compounds are useful for treating respiratory disorders, such as COPD and asthma. When used to treat such disorders, muscarinic receptor antagonists are typically administered by inhalation. However, even when administered by inhalation, a significant amount of the muscarinic receptor antagonist is often absorbed into the systemic circulation resulting in systemic side effects, such as dry mouth, mydriasis and cardiovascular side effects.

Additionally, many inhaled muscarinic receptor antagonists have a relatively short duration of action requiring that they be administered several times per day. Such a multiple-daily dosing regime is not only inconvenient but also creates a significant risk of inadequate treatment due to patient non-compliance with the required frequent dosing schedule.

Accordingly, a need exists for new muscarinic receptor antagonists. In particular, a need exists for new muscarinic receptor antagonists that having high potency and reduced systemic side effects when administered by inhalation. Additionally, a need exists for inhaled muscarinic receptor antagonists having a long duration of action thereby allowing for once-daily or even once-weekly dosing. Such compounds are expected to be particularly effective for treating pulmonary disorders, such as COPD and asthma, while reducing or eliminating side effects, such as dry-mouth and constipation.

SUMMARY OF THE INVENTION

The present invention provides novel biphenyl compounds having muscarinic receptor antagonist or anticholinergic activity. Among other properties, compounds of this invention have been found to possess high potency and reduced systemic side effects when administered by inhalation and to have a long duration of action.

Accordingly, in one of its composition aspects, this invention provides a compound of formula I:

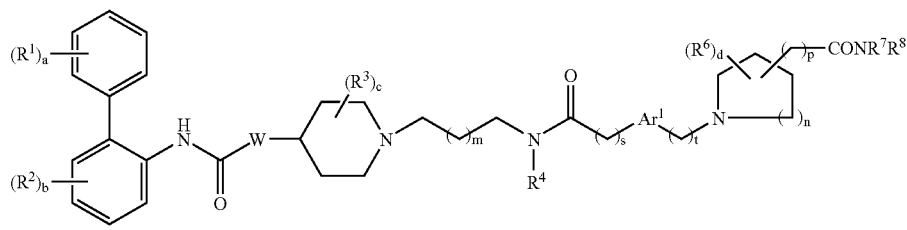

wherein:

a is 0 or an integer of from 1 to 5;

each $R^1$ is independently selected from (1-4C)alkyl, (2-4C)alkenyl, (2-4C)alkynyl, (3-6C)cycloalkyl, cyano, halo, —$OR^{1a}$, —$C(O)OR^{1b}$, —$SR^{1c}$, —$S(O)R^{1d}$, —$S(O)_2R^{1e}$, —$NR^{1f}R^{1g}$, —$NR^{1h}S(O)_2R^{1i}$, and —$NR^{1j}C(O)R^{1k}$; where each of $R^{1a}, R^{1b}, R^{1c}, R^{1d}, R^{1e}, R^{1f}, R^{1g}, R^{1h}, R^{1i}, R^{1j}$, and $R^{1k}$ is independently hydrogen, (1-4C)alkyl or phenyl(1-4C)alkyl;

b is 0 or an integer of from 1 to 4;

each $R^2$ is independently selected from (1-4C)alkyl, (2-4C)alkenyl, (2-4C)alkynyl, (3-6C)cycloalkyl, cyano, halo, —$OR^{2a}$, —$C(O)OR^{2b}$, —$SR^{2c}$, —$S(O)R^{2d}$, —$S(O)_2R^{2e}$, —$NR^{2f}R^{2g}$, —$NR^{2h}S(O)_2R^{2i}$, and —$NR^{2j}C(O)R^{2k}$; where each of $R^{2a}, R^{2b}, R^{2c}, R^{2d}, R^{2e}, R^{2f}, R^{2g}, R^{2h}, R^{2i}, R^{2j}$, and $R^{2k}$ is independently hydrogen, (1-4C)alkyl or phenyl(1-4C)alkyl;

W represents O or $NW^a$, where $W^a$ is hydrogen or (1-4C)alkyl;

c is 0 or an integer from 1 to 5;

each $R^3$ independently represents (1-4C)alkyl or two $R^3$ groups are joined to form (1-3C)alkylene, (2-3C)alkenylene or oxiran-2,3-diyl;

m is 0 or 1;

$R^4$ is selected from hydrogen, (1-4C)alkyl, and (3-4C)cycloalkyl;

s is 0, 1 or 2;

$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_q$ where q is 0 or an integer from 1 to 4 and each $R^5$ is independently selected from halo, hydroxy, (1-4C)alkyl or (1-4C)alkoxy;

t is 0, 1 or 2;

n is 0 or an integer from 1 to 3;

d is 0 or an integer from 1 to 4;

each $R^6$ independently represents fluoro or (1-4C)alkyl;

p is 0 or 1; and $R^7$ and $R^8$ are independently hydrogen or (1-4C)alkyl;

wherein each alkyl and alkoxy group in $R^1$, $R^{1a-1k}$, $R^2$, $R^{2a-2k}$, $R^3$, $R^5$, $R^6$, $R^7$, and $R^8$ is optionally substituted with 1 to 5 fluoro substituents;

or a pharmaceutically acceptable salt or solvate or stereoisomer thereof.

In another of its composition aspects, this invention is directed to a pharmaceutical composition comprising a pharmaceutically acceptable carrier and a therapeutically effective amount of a compound of formula I or a pharmaceutically acceptable salt or solvate or stereoisomer thereof. Such pharmaceutical compositions may optionally contain other therapeutic agents. Accordingly, in one embodiment, this invention is directed to such a pharmaceutical composition wherein the composition further comprises a therapeutically effective amount of a steroidal anti-inflammatory agent, such as a corticosteroid; a $\beta_2$ adrenergic receptor agonist; a phosphodiesterase-4 inhibitor; or a combination thereof.

Compounds of this invention possess muscarinic receptor antagonist activity. Accordingly, compounds of formula I are expected to be useful for treating pulmonary disorders, such as chronic obstructive pulmonary disease and asthma.

Accordingly, in one of its method aspects, this invention is directed to a method for treating a pulmonary disorder, the method comprising administering to a patient a therapeutically effective amount of a compound of formula I or a pharmaceutically acceptable salt or solvate or stereoisomer thereof.

Additionally, in another of its method aspects, this invention is directed to a method of producing bronchodilation in a patient, the method comprising administering to a patient a bronchodilation-producing amount of a compound of formula I or a pharmaceutically acceptable salt or solvate or stereoisomer thereof.

This invention is also directed to a method of treating chronic obstructive pulmonary disease or asthma, the method comprising administering to a patient a therapeutically effective amount of a compound of formula I or a pharmaceutically acceptable salt or solvate or stereoisomer thereof.

In another one of its method aspects, this invention is directed to a method for antagonizing a muscarinic receptor in a mammal comprising administering to the mammal, a therapeutically effective amount of the compound of formula I.

Since compounds of this invention possess muscarinic receptor antagonist activity, such compounds are also useful as research tools. Accordingly, in yet another of its method aspects, this invention is directed to a method for using a compound of formula I or a pharmaceutically acceptable salt or solvate or stereoisomer thereof as a research tool for studying a biological system or sample, or for discovering new chemical compounds having muscarinic receptor antagonist activity.

This invention is also directed to processes and novel intermediates useful for preparing compounds of formula I or a pharmaceutically acceptable salt or solvate or stereoisomer thereof. Accordingly, in another of its method aspects, this invention is directed to a process of preparing a compound of formula I, the process comprising:

(a) reacting a compound of formula II with a compound of formula III; or (b) coupling a compound of formula IV with a compound of formula V; or (c) reacting a compound of formula VI with a compound of formula VII; or (d) reacting a compound of formula II with a compound of formula VIII in the presence of a reducing agent; or (e) reacting a compound of formula IX with a compound of formula VII in the presence of a reducing agent; or (f) reacting a compound of formula XVIII with a compound of formula XIX;

and then removing any protecting groups, if necessary, to provide a compound of formula I; wherein compounds of formula I-IX, XVIII and XIX, are as defined herein.

In one embodiment, the above process further comprises the step of forming a pharmaceutically acceptable salt of a compound of formula I. In other embodiments, this invention is directed to the other processes described herein; and to the product prepared by any of the processes described herein.

This invention is also directed to a compound of formula I or a pharmaceutically acceptable salt or solvate or stereoisomer thereof, for use in therapy or as a medicament.

Additionally, this invention is directed to the use of a compound of formula I or a pharmaceutically acceptable salt or solvate or stereoisomer thereof, for the manufacture of a medicament; especially for the manufacture of a medicament for the treatment of a pulmonary disorder or for antagonizing a muscarinic receptor in a mammal.

DETAILED DESCRIPTION OF THE INVENTION

In one of its composition aspects, this invention is directed to novel biphenyl compounds of formula I or pharmaceutically acceptable salts or solvates or stereoisomers thereof. These compounds may contain one or more chiral centers and therefore, this invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of this invention unless otherwise indicated, provided that the desired utility of the composition as a whole is not eliminated by the presence of such other isomers.

The compounds of formula I also contain several basic groups (e.g., amino groups) and therefore, the compounds of formula I can exist as the free base or in various salt forms. All such salt forms are included within the scope of this invention. Furthermore, solvates of compounds of formula I or salts thereof are included within the scope of this invention.

Additionally, where applicable, all cis-trans or E/Z isomers (geometric isomers), tautomeric forms and topoisomeric forms of the compounds of formula I are included within the scope of this invention unless otherwise specified.

The compounds of formula I, as well as those compounds used in its synthesis, may also include isotopically-labeled compounds, i.e., where one or more atoms have been enriched with atoms having an atomic mass different from the atomic mass predominately found in nature. Examples of isotopes that may be incorporated into the compounds of Formula (I) include, but are not limited to, $^2H$, $^3H$, $^{13}C$, $^{14}C$, $^{15}N$, $^{18}O$ and $^{17}O$.

The nomenclature used herein to name the compounds of this invention is illustrated in the Examples herein. This nomenclature has been derived using the commercially-available AutoNom software (MDL, San Leandro, Calif.). For example, compounds of formula I wherein W is O have typically been named as ester derivatives of biphenyl-2-ylcarbamic acid.

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

The value for a is 0, 1, 2, 3, 4 or 5; particularly 0, 1 or 2, and even more particularly 0 or 1. The value for b is 0, 1, 2, 3 or 4; particularly 0, 1 or 2, and even more particularly 0 or 1. In one embodiment, both a and b are 0.

When present, each $R^1$ may be at the 2, 3, 4, 5 or 6-position of the phenyl ring to which it is attached. Each $R^1$ is independently selected from (1-4C)alkyl, (2-4C)alkenyl, (2-4C)alkynyl, (3-6C)cycloalkyl, cyano, halo, —$OR^{1a}$, —$C(O)OR^{1b}$, —$SR^{1c}$, —$S(O)R^{1d}$, —$S(O)_2R^{1e}$, —$NR^{1f}R^{1g}$, —$NR^{1h}S(O)_2R^{1i}$, and —$NR^{1j}C(O)R^{1k}$, examples of which include methyl, fluoro, chloro, bromo, hydroxy, methoxy, amino, methylamino, dimethylamino and the like. Particular values for $R^1$ are fluoro or chloro.

When present, each $R^2$ may be at the 3, 4, 5 or 6-position on the phenylene ring to which it is attached (where the carbon atom on the phenylene ring attached to the nitrogen atom is position 1). Each $R^2$ is independently selected from (1-4C)alkyl, (2-4C)alkenyl, (2-4C)alkynyl, (3-6C)cycloalkyl, cyano, halo, —$OR^{2a}$, —$C(O)OR^{2b}$, —$SR^{2c}$, —$S(O)R^{2d}$, —$S(O)_2R^{2e}$, —$NR^{2f}R^{2g}$, —$NR^{2h}S(O)_2R^{2i}$, and —$NR^{2j}C(O)R^{2k}$, examples of which include methyl, fluoro, chloro, bromo, hydroxy, methoxy, amino, methylamino, dimethylamino and the like. Particular values for $R^2$ are fluoro or chloro.

Each $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$ and $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$ as used in $R^1$ and $R^2$, respectively, is independently hydrogen, (1-4C)alkyl or phenyl(1-4C)alkyl, examples of which include hydrogen, methyl, ethyl, n-propyl, isopropyl, n-butyl, sec-butyl, isobutyl, tert-butyl or benzyl. In one embodiment, these groups are independently hydrogen or (1-3C)alkyl. In another embodiment, these groups are independently hydrogen, methyl or ethyl. In addition, each alkyl and alkoxy group in $R^1$, $R^{1a-1k}$, $R^2$, and $R^{2a-2k}$ is optionally substituted with 1 to 5 fluoro substituents.

In one embodiment of this invention, W is O. In another embodiment, W is $NW^a$. Generally, it has been found that compounds in which W represents O exhibit particularly high affinity for muscarinic receptors. Accordingly, in a particular embodiment of this invention, W represents O.

When W is $NW^a$, $W^a$ is hydrogen or (1-4C)alkyl, examples of which include hydrogen, methyl, ethyl, n-propyl, isopropyl, n-butyl, sec-butyl, isobutyl and tert-butyl. In one embodiment, $W^a$ is hydrogen or (1-3C)alkyl. In another embodiment, $W^a$ is hydrogen, methyl or ethyl, particularly hydrogen or methyl. In yet another embodiment, $W^a$ is hydrogen and $NW^a$ is NH.

The value for c is 0, 1, 2, 3, 4, or 5; particularly 0, 1, or 2; and more particularly 0 or 1. In one particular embodiment, c is 0. In another embodiment, c is 2.

Each $R^3$ independently represents (1-4C)alkyl or two $R^3$ groups that are joined to form (1-3C)alkylene, (2-3C)alkenylene or oxiran-2,3-diyl. In one embodiment, each $R^3$ is independently (1-4C)alkyl, such as methyl, ethyl, n-propyl, isopropyl, n-butyl, sec-butyl, isobutyl and tert-butyl. In addition, each alkyl group in $R^3$ is optionally substituted with 1 to 5 fluoro substituents. In one embodiment, each $R^3$ is independently (1-3C)alkyl, and in another embodiment, each $R^3$ is independently methyl or ethyl.

In one embodiment, each $R^3$ is at the 3, 4 or 5-position on the piperidine ring (where the nitrogen atom of the piperidine ring is position 1). In a particular embodiment, $R^3$ is at the 4-position on the piperidine ring. In another embodiment, $R^3$ is at the 1-position of the piperidine ring, i.e., on the nitrogen atom of the piperidine ring thus forming a quaternary amine salt.

In yet another embodiment, two $R^3$ groups are joined to form a (1-3C)alkylene or (2-3C)alkenylene group. For example, two $R^3$ groups at the 2 and 6-positions on the piperidine ring can be joined to form an ethylene bridge (i.e., the piperidine ring and the $R^3$ groups form an 8-azabicyclo[3.2.1]octane ring); or two $R^3$ groups at the 1 and 4-positions on the piperidine ring can be joined to form an ethylene bridge (i.e., the piperidine ring and the $R^3$ groups form an 1-azabicyclo[2.2.2]octane ring). In this embodiment, other $R^3$ groups as defined herein may also be present.

In still another embodiment, two $R^3$ groups are joined to form a oxiran-2,3-diyl group. For example, two $R^3$ groups at the 2 and 6-positions on the piperidine ring can be joined to form a 3-oxatricyclo[3.3.1.0$^{2,4}$]nonane ring). In this embodiment, other $R^3$ groups as defined herein may also be present.

The value for m is 0 or 1. In one embodiment, m is 0.

$R^4$ represents hydrogen, (1-4C)alkyl, or (3-4C)cycloalkyl. Examples of (1-4C)alkyl include methyl, ethyl, n-propyl, isopropyl, n-butyl, sec-butyl, isobutyl and tert-butyl. Examples of (3-4C)cycloalkyl groups include cyclopropyl and cyclobutyl. In one embodiment $R^4$ represents hydrogen or (1-3C)alkyl, in particular hydrogen, methyl or ethyl. In another embodiment, $R^4$ is hydrogen.

The value for s is 0, 1 or 2. A particular value for s is 0 or 1. In one embodiment, s is 0. In another embodiment, s is 2.

$Ar^1$ is a phenylene group or a (3-5C)heteroarylene group containing 1 or 2 heteroatoms independently selected from oxygen, nitrogen or sulfur. The phenylene or heteroarylene group may be unsubstituted (q is 0) or substituted with 1, 2, 3, or 4 (q is 1, 2, 3, or 4) $R^5$ substituents, which are independently selected from halo, hydroxy, (1-4C)alkyl or (1-4C)alkoxy. In addition, each alkyl and alkoxy group in $R^5$ is optionally substituted with 1 to 5 fluoro substituents. The value for q is 0, 1, 2, 3, or 4, particularly 0, 1, 2 or 3. In one embodiment, q is 0, 1 or 2. The point of attachment for $Ar^1$ is at any available carbon or heteroatom ring atom. In certain embodiments, $Ar^1$ is a phenylene group attached at the meta or para position.

In one embodiment $Ar^1$ is phen-1,3-ylene or phen-1,4-ylene wherein the phenylene group is unsubstituted or substituted with 1, 2 or 3 $R^5$ substituents. Representative $R^5$ substituents include fluoro, chloro, bromo, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of $Ar^1$ groups in this embodiment include 2-fluorophen-1,4-ylene, 3-fluorophen-1,4-ylene, 2-chlorophen-1,4-ylene, 3-chlorophen-1,4-ylene, 2-methylphen-1,4-ylene, 3-methylphen-1,4-ylene, 2-methoxyphen-1,4-ylene, 3-methoxyphen-1,4-ylene, 2-trifluoromethoxyphen-1,4-ylene, 3-trifluoromethoxyphen-1,4-ylene, 2,3-difluorophen-1,4-ylene, 2,5-difluorophen-1,4-ylene, 2,6-difluorophen-1,4-ylene, 2,3-dichlorophen-1,4-ylene, 2,5-dichlorophen-1,4- ylene, 2,6-dichlorophen-1,4-ylene, 2-chloro-5-methoxyphen-1,4-ylene, 2-chloro-6-methoxyphen-1,4-ylene, 2-chloro-5-trifluoromethoxyphen-1,4-ylene, 2-chloro-6-trifluoromethoxyphen-1,4-ylene, and 2,5-dibromophen-1,4-ylene.

In another embodiment, $Ar^1$ is a (3-5C)heteroarylene group containing 1 or 2 heteroatoms independently selected from oxygen, nitrogen or sulfur; wherein the heteroarylene group is unsubstituted or substituted with 1 or 2 $R^5$ substituents. Representative heteroarylene groups include divalent species of pyrrole, imidazole, thiazole, oxazole, furan, thiophene, pyrazole, isoxazole, isothiazole, pyridine, pyrazine, pyridazine and pyrimidine, where the point of attachment is at any available carbon or nitrogen ring atom. More specific examples of such $Ar^1$ groups include 2,5-furylene, 2,4-thienylene, 2,5-thienylene, 2,5-pyridylene, 2,6-pyridylene, and 2,5-pyrrolylene. Representative $R^5$ substituents include fluoro, chloro, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of substituted $Ar^1$ groups include 3-fluoro-2,5-thienylene, 3-chloro-2,5-thienylene, 3-methyl-2,5-thienylene, 3-methoxy-2,5-thienylene, and 3-methoxy-6-chloro-2,5-pyridylene.

In one particular embodiment, $Ar^1$ represents phen-1,3-ylene, phen-1,4-ylene, 2,4-thienylene or 2,5-thienylene; wherein the phenylene or thienylene group is optionally substituted with 1 or 2 $R^5$ substituents. In another particular embodiment, $Ar^1$ represents phen-1,4-ylene or 2,4-thienylene optionally substituted with 1 or 2 $R^5$ substituents.

The value for t is 0, 1 or 2. A particular value for t is 1.

The value for n is 0, 1, 2, or 3. Particular values for n are 1 or 2. In one embodiment, n is 2.

The value for d is 0, 1, 2, 3, or 4. Particular values for d are 0, 1 or 2. In one embodiment, d is 0.

Each $R^6$ independently represents fluoro or (1-4C)alkyl, examples of which include methyl, ethyl, n-propyl, isopropyl, n-butyl, sec-butyl, isobutyl and tert-butyl. In addition, each alkyl and alkoxy group in $R^6$ is optionally substituted with 1 to 5 fluoro substituents. In one embodiment, each $R^6$ independently represents fluoro or (1-3C)alkyl, and in another embodiment, each $R^6$ is independently selected from fluoro, methyl, ethyl or trifluoromethyl.

The value for p is 0 or 1. In one particular embodiment, p is 0.

$R^7$ and $R^8$ each independently represent hydrogen or (1-4C)alkyl, examples of which include methyl, ethyl, n-propyl, isopropyl, n-butyl, sec-butyl, isobutyl and tert-butyl. In one embodiment, $R^7$ and $R^8$ each independently represent hydrogen or (1-3C)alkyl. In a particular embodiment, $R^7$ is hydrogen, methyl, ethyl, n-propyl or isopropyl, and $R^8$ is hydrogen. In another particular embodiment, $R^7$ and $R^8$ are both hydrogen or both ethyl. In addition, each alkyl and alkoxy group in $R^7$ and $R^8$ is optionally substituted with 1 to 5 fluoro substituents.

As noted in formula I, the —$CONR^7R^8$ group can be located at any carbon atom on the ring. For example, when n is 2, the —$CONR^7R^8$ group can be located at the ortho, meta or para position. In one embodiment, the —$CONR^7R^8$ group is located at the meta or para position; and in a particular embodiment, the —$CONR^7R^8$ group is located at the para position.

A particular group of compounds of interest are compounds of formula I wherein a, b, c and d are 0; n is 2; and $R^4$ is hydrogen, methyl or ethyl.

Another particular group of compounds of interest are compounds of formula I wherein a, b, c and d are 0; $R^4$ is hydrogen, methyl or ethyl; and $R^7$ is hydrogen.

Another particular group of compounds of interest are compounds of formula I wherein a, b, c and d are 0; $R^4$ is hydrogen, methyl or ethyl; $R^7$ is hydrogen, methyl, ethyl, n-propyl or isopropyl, and $R^8$ is hydrogen.

Another particular group of compounds of interest are compounds of formula I wherein a, b, c and d are 0; $R^4$ is hydrogen, methyl or ethyl; and $R^7$ and $R^8$ are ethyl.

Another particular group of compounds of interest are compounds of formula I wherein a, b, c and d are 0; $R^4$ is hydrogen, methyl or ethyl; $R^7$ and $R^8$ are hydrogen; and s is 0.

Another particular group of compounds of interest are compounds of formula I wherein a, b, c and d are 0; $R^4$ is hydrogen, methyl or ethyl; $R^7$ and $R^8$ are hydrogen; s is 0; and t is 1.

Another particular group of compounds of interest are compounds of formula I wherein a, b, c and d are 0; $R^4$ is hydrogen, methyl or ethyl; $R^7$ and $R^8$ are hydrogen; s is 0; t is 1; and m is 0.

Representative Subgeneric Groupings

The following subgeneric formulae and groupings are intended to provide representative examples of various aspects and embodiments of this invention and as such, they are not intended to exclude other embodiments or to limit the scope of this invention unless otherwise indicated.

A particular group of compounds of formula I are those disclosed in U.S. Provisional Application No. 60/552,443, filed on Mar. 11, 2004. This group includes compounds of formula Ia:

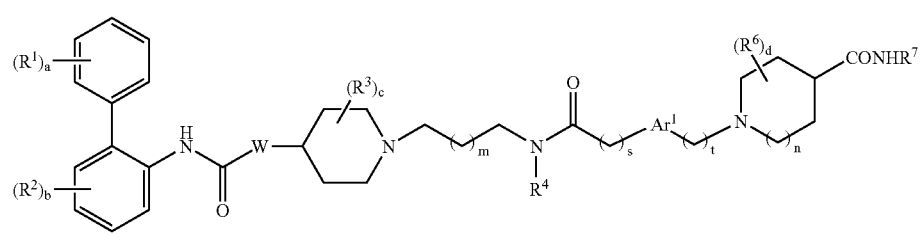

Ia wherein:
a is 0 or an integer of from 1 to 3; each $R^1$ is independently selected from (1-4C)alkyl, (2-4C)alkenyl, (2-4C)alkynyl, (3-6C)cycloalkyl, cyano, halo, —$OR^{1a}$, —$C(O)OR^{1b}$, —$SR^{1c}$, —$S(O)R^{1d}$, —$S(O)_2R^{1e}$ and —$NR^{1f}R^{1g}$; each of $R^{1a}$, $R^{1b}$, $R^{1c}$, $R^{1d}$, $R^{1e}$, $R^{1f}$ and $R^{1g}$ is independently hydrogen, (1-4C)alkyl or phenyl(1-4C)alkyl;

b is 0 or an integer of from 1 to 3; each $R^2$ is independently selected from (1-4C)alkyl, (2-4C)alkenyl, (2-4C)alkynyl, (3-6C)cycloalkyl, cyano, halo, —$OR^{2a}$, —$C(O)OR^{2b}$, —$SR^{2c}$, —$S(O)R^{2d}$, —$S(O)_2R^{2e}$ and —$NR^{2f}R^{2g}$; each of $R^{2a}$, $R^{2b}$, $R^{2c}$, $R^{2d}$, $R^{2e}$, $R^{2f}$ and $R^{2g}$ is independently hydrogen, (1-4C)alkyl or phenyl(1-4C)alkyl;

W represents O or $NW^a$, where $W^a$ is hydrogen or (1-4C)alkyl;

c is 0 or an integer from 1 to 4; each $R^3$ independently represents (1-4C)alkyl;

m is 0 or 1;

$R^4$ is hydrogen or (1-4C)alkyl;

s is 0 or 1;

$Ar^1$ represents a phenylene group or a (3-5C)heteroarylene group containing 1 or 2 heteroatoms selected independently from oxygen, nitrogen or sulfur; wherein the phenylene or heteroarylene group is substituted with $(R^5)_q$ where q is 0 or an integer from 1 to 4 and each $R^5$ is selected independently from halo, hydroxy, (1-4C)alkyl or (1-4C)alkoxy;

t is 0 or 1;

n is 0, 1 or 2;

d is 0 or an integer from 1 to 4; each $R^6$ independently represents fluoro or (1-4C)alkyl; and $R^7$ is hydrogen or (1-4C)alkyl;

wherein each alkyl and alkoxy group in $R^1$, $R^{1a-1g}$, $R^2$, $R^{2a-2g}$, $R^3$, $R^5$, $R^6$ or $R^7$ is optionally substituted with 1 to 5 fluoro substituents; or a pharmaceutically acceptable salt or solvate or stereoisomer thereof.

This group also includes compounds of formula Ib:

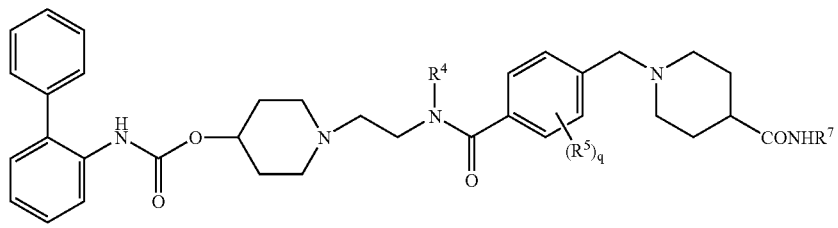

Ib wherein: $R^4$, q, $R^5$ and $R^7$ are as defined for formula Ia; or a pharmaceutically acceptable salt or solvate or stereoisomer thereof. A particular embodiment includes compounds of formula Ib, where q is 0, 1 or 2, and $R^5$ is independently selected from halo, (1-4C)alkyl or (1-4C)alkoxy, wherein each alkyl and alkoxy group is optionally substituted with from 1 to 3 fluoro substituents.

In addition, particular compounds of formula I that are of interest include:

biphenyl-2-ylcarbamic acid 1-(2-{[4-(4-carbamoylpiperidin-1-ylmethyl)benzoyl]methylamino}ethyl)piperidin-4-yl ester;

biphenyl-2-ylcarbamic acid 1-(2-{[4-(4-carbamoylpiperidin-1-ylmethyl)benzoyl]ethylamino}ethyl)piperidin-4-yl ester;

biphenyl-2-ylcarbamic acid 1-(2-{methyl-[4-(4-methylcarbamoylpiperidin-1-ylmethyl)benzoyl]amino}ethyl)piperidin-4-yl ester;

biphenyl-2-ylcarbamic acid 1-(2-{[4-(4-ethylcarbamoylpiperidin-1-ylmethyl)benzoyl]methylamino}ethyl)piperidin-4-yl ester;

biphenyl-2-ylcarbamic acid 1-(2-{methyl-[4-(4-propylcarbamoylpiperidin-1-ylmethyl)benzoyl]amino}ethyl)piperidin-4-yl ester;

biphenyl-2-ylcarbamic acid 1-(2-{[4-(4-isopropylcarbamoylpiperidin-1-ylmethyl)benzoyl]methylamino}ethyl)piperidin-4-yl ester;

biphenyl-2-ylcarbamic acid 1-{2-[4-(4-carbamoylpiperidin-1-ylmethyl)-2-fluorobenzoylamino]ethyl}piperidin-4-yl ester;

biphenyl-2-ylcarbamic acid 1-(2-{[2,5-dibromo-4-(4-carbamoylpiperidin-1-ylmethyl)benzoyl]methylamino}ethyl)piperidin-4-yl ester;

biphenyl-2-ylcarbamic acid 1-(2-{[4-(4-carbamoylpiperidin-1-ylmethyl)-2-fluorobenzoyl]methylamino}ethyl)piperidin-4-yl ester;

biphenyl-2-ylcarbamic acid 1-{2-[4-(4-diethylcarbamoylpiperidin-1-ylmethyl)-2-fluorobenzoylamino]ethyl}piperidin-4-yl ester;

biphenyl-2-ylcarbamic acid 1-(2-{[4-(4-diethylcarbamoylpiperidin-1-ylmethyl)-2-fluorobenzoyl]methylamino}ethyl)piperidin-4-yl ester;

biphenyl-2-ylcarbamic acid 1-(2-{[4-(4-diethylcarbamoylpiperidin-1-ylmethyl)benzoyl]methylamino}ethyl)piperidin-4-yl ester;

biphenyl-2-ylcarbamic acid 1-(2-{[4-(3-(S)-diethylcarbamoylpiperidin-1-ylmethyl)benzoyl]methylamino}ethyl)piperidin-4-yl ester;

biphenyl-2-yl-carbamic acid 1-(2-{[4-(2-carbamoyl-piperidin-1-ylmethyl)benzoyl]methylamino}ethyl)piperidin-4-yl ester;

biphenyl-2-yl-carbamic acid 1-(2-{[4-(4-carbamoyl-piperidin-1-ylmethyl)-2-methoxybenzoyl]methylamino}ethyl)piperidin-4-yl ester;

biphenyl-2-yl-carbamic acid 1-(2-{[5-(4-carbamoylpiperidin-1-ylmethyl)thiophene-2-carbonyl]methylamino}ethyl)piperidin-4-yl ester;

biphenyl-2-yl-carbamic acid 1-(2-{[5-((R)-3-diethylcarbamoylpiperidin-1-ylmethyl)thiophene-2-carbonyl]methylamino}ethyl)piperidin-4-yl ester;

biphenyl-2-yl-carbamic acid 1-(2-{[5-((R)-3-diethylcarbamoylpiperidin-1-ylmethyl)thiophene-2-carbonyl]amino}ethyl)piperidin-4-yl ester;

biphenyl-2-yl-carbamic acid 1-(2-{[5-(4-carbamoylpiperidin-1-ylmethyl)thiophene-2-carbonyl]amino}ethyl)piperidin-4-yl ester;
biphenyl-2-yl-carbamic acid 1-(2-{[5-((R)-3-diethylcarbamoylpiperidin-1-ylmethyl)-1H-pyrrole-2-carbonyl] methylamino}ethyl)piperidin-4-yl ester;
biphenyl-2-yl-carbamic acid 1-(2-{[5-(4-carbamoylpiperidin-1-ylmethyl)-1H-pyrrole-2-carbonyl] methylamino}ethyl)piperidin-4-yl ester;
biphenyl-2-yl-carbamic acid 1-(2-{[5-((R)-3-diethylcarbamoylpiperidin-1-ylmethyl)furan-2-carbonyl] methylamino}ethyl)piperidin-4-yl ester;
biphenyl-2-yl-carbamic acid 1-(2-{[5-(4-diethylcarbamoylpiperidin-1-ylmethyl)furan-2-carbonyl] methylamino}ethyl)piperidin-4-yl ester;
biphenyl-2-yl-carbamic acid 1-(2-{[5-(4-carbamoylpiperidin-1-ylmethyl)furan-2-carbonyl]-amino}ethyl)piperidin-4-yl ester;
biphenyl-2-yl-carbamic acid 1-(2-{[5-((R)-3-diethylcarbamoylpiperidin-1-ylmethyl)furan-2-carbonyl]amino}ethyl) piperidin-4-yl ester;
biphenyl-2-yl-carbamic acid 1-[2-({3-[4-(3-carbamoylpiperidin-1-ylmethyl)phenyl]propionyl}methylamino)ethyl] piperidin-4-yl ester;
biphenyl-2-yl-carbamic acid 1-[2-({3-[4-(4-carbamoylpiperidin-1-ylmethyl)phenyl]propionyl}methylamino)ethyl] piperidin-4-yl ester;
biphenyl-2-yl-carbamic acid 1-(2-{3-[4-(4-carbamoylpiperidin-1-ylmethyl)phenyl]propionylamino}ethyl)piperidin-4-yl ester;
biphenyl-2-yl-carbamic acid 1-(2-{3-[4-(4-diethylcarbamoylpiperidin-1-ylmethyl)phenyl]propionylamino}ethyl) piperidin-4-yl ester;
biphenyl-2-yl-carbamic acid 1-(2-{3-[4-(3-diethylcarbamoylpiperidin-1-ylmethyl)phenyl]propionylamino}ethyl) piperidin-4-yl ester;
biphenyl-2-ylcarbamic acid 1-{2-[4-(4-carbamoylpiperidin-1-ylmethyl)benzoylamino]ethyl}piperidin-4-yl ester;
biphenyl-2-ylcarbamic acid 1-(2-{[4-(4-carbamoylpiperidin-1-ylmethyl)-2-chloro-benzoyl]methylamino}ethyl) piperidin-4-yl ester;
biphenyl-2-ylcarbamic acid 1-(2-{[4-(4-carbamoylpiperidin-1-ylmethyl)-2-chloro-5-methoxybenzoyl] methylamino}ethyl)piperidin-4-yl ester; and
biphenyl-2-ylcarbamic acid 1-[2-({2-[4-(4-carbamoylpiperidin-1-ylmethyl)phenyl]acetyl}methylamino)ethyl]piperidin-4-yl ester;

or a pharmaceutically acceptable salt or solvate thereof.

Definitions

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "azacycloalkyl" means a monovalent heterocyclic ring containing one nitrogen atom, i.e., a cycloalkyl group in which one carbon atom has been replaced with a nitrogen atom. Unless otherwise defined, such azacycloalkyl groups typically contain from 2 to 9 carbon atoms. Representative examples of an azacycloalkyl group are pyrrolidinyl and piperidinyl groups. The term "azacycloalkylene" means a divalent azacycloalkyl group. Representative examples of an azacycloalkylene group are pyrrolidinylene and piperidinylene groups.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group.

When a specific number of carbon atoms is intended for a particular term used herein, the number of carbon atoms is shown in parentheses preceding the term. For example, the term "(1-4C)alkyl" means an alkyl group having from 1 to 4 carbon atoms.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers, such as a solvate of a pharmaceutically acceptable salt of a stereoisomer of a compound of formula I.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:
  (a) preventing the disease or medical condition from occurring, i.e., prophylactic treatment of a patient;
  (b) ameliorating the disease or medical condition, i.e., eliminating or causing regression of the disease or medical condition in a patient;
  (c) suppressing the disease or medical condition, i.e., slowing or arresting the development of the disease or medical condition in a patient; or
  (d) alleviating the symptoms of the disease or medical condition in a patient.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluoroenylmethyl (Fm), trimethylsilyl (TMS), tert-butyldimethylsilyl (TBS), diphenylmethyl (benzhydryl, DPM) and the like.

The term "hydroxyl-protecting group" means a protecting group suitable for preventing undesirable reactions at a hydroxyl group. Representative hydroxyl-protecting groups include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C)alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

General Synthetic Procedures

The biphenyl compounds of this invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

By way of illustration, the compounds of formula I can be prepared by a process comprising:

(a) reacting a compound of formula II:

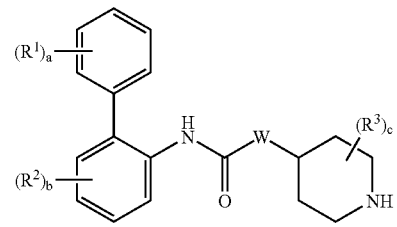

II or a salt thereof, with a compound of formula III:

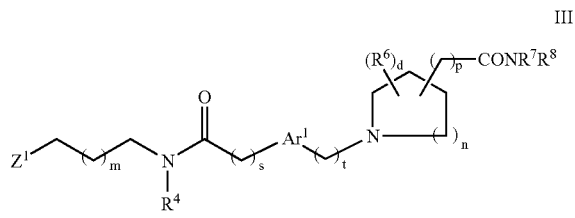

III wherein $Z^1$ represents a leaving group; or (b) coupling a compound of formula IV:

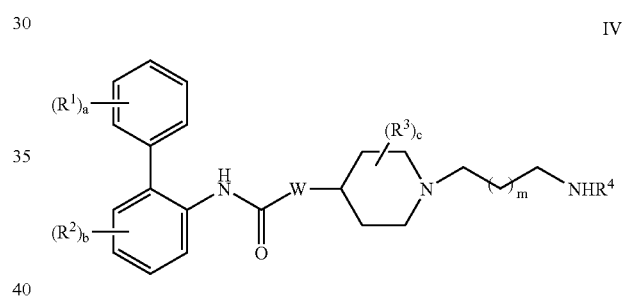

IV with a compound of formula V:

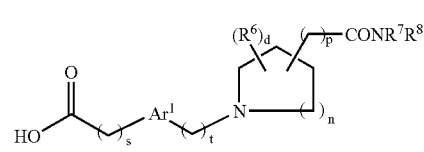

V or a reactive derivative thereof; or (c) reacting a compound of formula VI:

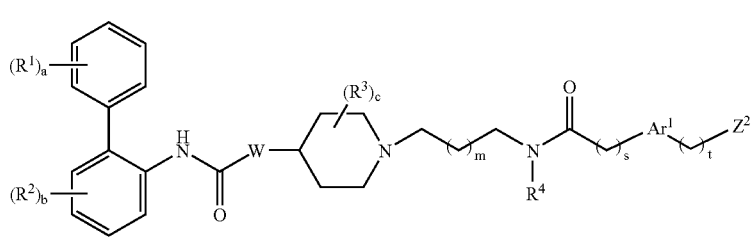

VI wherein $Z^2$ represents a leaving group; with a compound of formula VII:

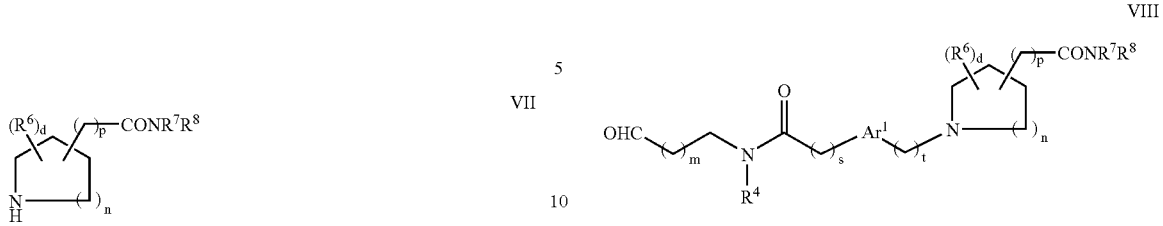

or (d) reacting a compound of formula II with a compound of formula VIII:

in the presence of a reducing agent; or (e) reacting a compound of formula IX:

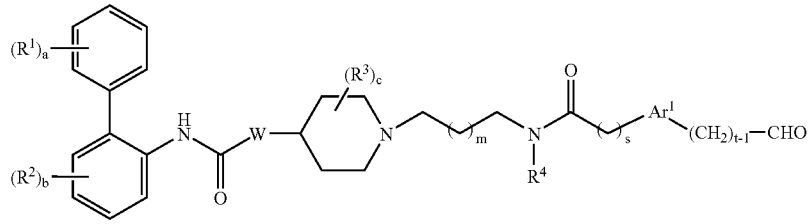

with a compound of formula VII in the presence of a reducing agent; or (f) reacting a compound of formula XVIII:

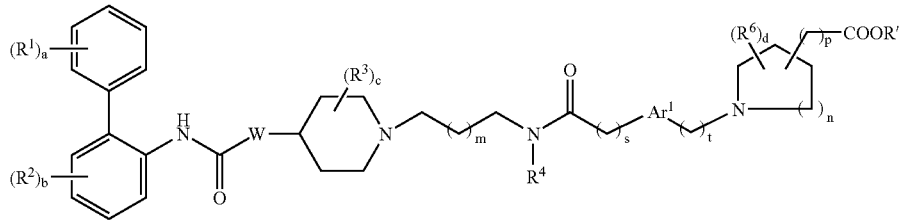

where R' is H, —CH$_3$ or —CH$_2$CH$_3$, with a compound of formula XIX:

NHR$^7$R$^8$      XIX and then (g) removing any protecting groups that may be present to provide a compound of formula I; and optionally, forming a pharmaceutically acceptable salt thereof.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

In process (a), the reaction between the compounds of formula II and III, the leaving represented by $Z^1$ can be, for example, halo, such as chloro, bromo or iodo, or a sulfonic ester group, such as mesylate or tosylate. The reaction is conveniently performed in the presence of a base, for example, a tertiary amine such as diisopropylethylamine. Convenient solvents include nitriles, such as acetonitrile. The reaction is conveniently conducted at a temperature in the range of from 0° C. to 100° C.

Compounds of formula II are generally known in the art, or can be prepared by deprotecting a compound of formula X:

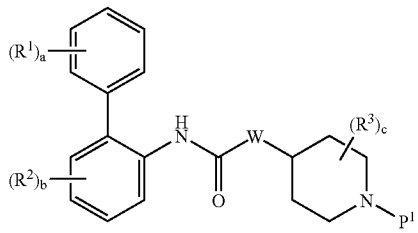

wherein $P^1$ represents an amino-protecting group, such as a benzyl group. Benzyl groups are conveniently removed by reduction, using a hydrogen or ammonium formate and a Group VIII metal catalyst, such as palladium. When W represents $NW^a$, the hydrogenation is conveniently performed using Pearlman's catalyst ($Pd(OH)_2$).

Compounds of formula X can be prepared by reacting an isocyanate compound of formula XI:

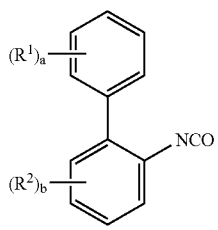

with a compound of formula XII:

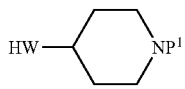

Compounds of formula III can be prepared starting from a corresponding compound in which $Z^1$ represents a hydroxyl group, for example, by reaction of a halogenating agent, such as thionyl chloride, to afford a compound of formula III in which $Z^1$ represents halo, such as chloro. Compounds in which $Z^1$ represents a hydroxyl group may be prepared, for example, by reacting a compound of formula V with an appropriate amino-substituted alcohol, such as 2-aminoethanol or 3-aminopropan-1-ol.

In process (b), a compound of formula IV is reacted with a compound of formula V or reactive derivative thereof. By "reactive derivative" of compound V, it is meant that the carboxylic acid is activated, for example, by forming an anhydride or carboxylic acid halide, such as a carboxylic acid chloride. Alternatively, the carboxylic acid can be activated using conventional carboxylic acid/amine coupling reagents, such carbodiimides, O-(7-azabenzotriazol-1-yl-N,N,N',N' tetramethyluronium hexafluorophosphate (HATU) and the like. This reaction is conveniently performed under conventional amide bond-forming conditions. The process is conveniently conducted at a temperature in the range of from −10° C. to 100° C.

Compounds of formula IV can be prepared by reacting a compound of formula II with a compound of formula XIII:

wherein $P^2$ represents hydrogen or an amino-protecting group, such as benzyl, in the presence of a reducing agent, such as sodium triacetoxyborohydride, followed if necessary by removing the amino-protecting group $P^2$ by, for example, hydrogenation in the presence of palladium.

Compounds of formula V can be prepared by reacting a compound of formula VII with a compound of formula XIV:

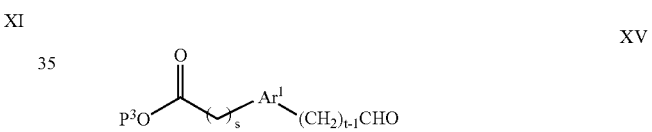

wherein $P^3$ represents hydrogen or a carboxyl-protecting group, such as methyl or ethyl, and $Z^3$ represents a leaving group, followed if necessary by removing the carboxyl protecting group $P^3$. Alternatively, such compounds can be prepared by reductive amination of a compound of formula XV:

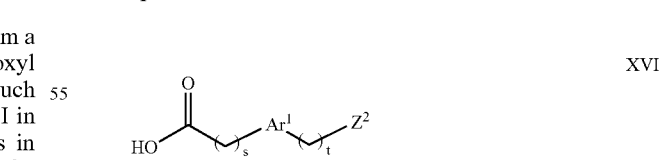

with a compound of formula VII under conventional reaction conditions, such as those described for processes (d) and (e).

Referring to process (c), the leaving group represented by $Z^2$ can be, for example, halo, such as chloro, bromo or iodo, or a sulfonic ester group, such as mesylate or tosylate. This reaction is conveniently performed in the presence of a base, for example, a tertiary amine such as diisopropylethylamine. Convenient solvents include nitrites, such as acetonitrile. The reaction is conveniently conducted at a temperature in the range of from 0° C. to 100° C. The compounds of formula VI can be prepared by reacting a compound of formula IV with a compound of formula XVI:

or a reactive derivative thereof, such as an acid chloride or anhydride. The reaction is conveniently performed following, for example, the method of process (b) described herein. Compounds of formula VII are generally known or can be prepared from readily available starting materials using well-known synthetic methods.

In process (d), the reducing agent may be, for example, hydrogen in the presence of a Group VIII metal catalyst, such as palladium, or a metal hydride reducing agent, such as a borohydride, including sodium triacetoxyborohydride. Convenient solvents include alcohols, such as methanol. The reaction is conveniently performed at a temperature in the range of from 0° C. to 100° C. The compounds of formula VIII may be prepared by oxidizing a compound corresponding to formula III in which $Z^1$ represents a hydroxyl group. Such oxidation reactions can be conducted, for example, using sulfur dioxide pyridine complex in dimethylsulfoxide in the presence of a tertiary amine, such as diisopropylethylamine.

In process (e), the reducing agent may be, for example, hydrogen in the presence of a Group VIII metal catalyst, such as palladium, or a metal hydride reducing agent including borohydrides, such as sodium triacetoxyborohydride, optionally used in combination with a titanium tetraalkoxide, such as titanium tetraisopropoxide. Convenient solvents include alcohols, such as methanol and halogenated hydrocarbons, such as dichloromethane. The reaction is conveniently performed at a temperature in the range of from 0° C. to 100° C. Compounds of formula IX may be prepared by reacting a compound of formula IV with a compound of formula XVII:

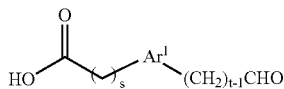

XVII in the presence of a carboxylic acid/amine coupling agent, such as 1-(3-dimethylaminopropyl)-3-ethylcarbodiimide (EDC) and 1-hydroxybenzotriazole hydrate (HOBT) and the like.

Referring to process (f), compounds of formula XVIII may be prepared by reacting a compound of formula IX with a compound of formula VII in the presence of a reducing agent, such as sodium triacetoxyborohydride, similar to that done in process (e).

As will be apparent to those skilled in the art, compounds of formula I prepared by any of steps (a) to (f) herein may be further derivatized to form other compounds of formula I using methods and reagents well-known in the art. By way of illustration, a compound of formula I may be reacted with bromine to afford a corresponding compound of formula I in which $R^2$, for example, represents a bromo group. Additionally, a compound of formula I in which $R^4$ represents a hydrogen atom may be alkylated to afford a corresponding compound of formula I in which $R^4$ represents a (1-4C) alkyl group.

Certain of the intermediates described herein are believed to be novel and accordingly, such compounds are provided as further aspects of the invention including, for example, the compounds of formula III, V, and VIII, and salts thereof.

Further details regarding specific reaction conditions and other procedures for preparing representative compounds of this invention or intermediates thereof are described in the Examples set forth below.

Pharmaceutical Compositions and Formulations

The biphenyl compounds of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration.

It will be understood that any form of the compounds of this invention, (i.e., free base, pharmaceutically acceptable salt, solvate, etc.) that is suitable for the particular mode of administration can be used in the pharmaceutical compositions discussed herein.

Accordingly, in one of its composition aspects, this invention is directed to a pharmaceutical composition comprising a pharmaceutically acceptable carrier or excipient and a therapeutically effective amount of a compound of formula I, or a pharmaceutically acceptable salt or solvate or stereoisomer thereof. Optionally, such pharmaceutical compositions may contain other therapeutic and/or formulating agents if desired.

The pharmaceutical compositions of this invention typically contain a therapeutically effective amount of a compound of the present invention or a pharmaceutically acceptable salt or solvate or stereoisomer thereof. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in Remington: The Science and Practice of Pharmacy, $20^{th}$ Edition, Lippincott Williams & White, Baltimore, Md. (2000); and H. C. Ansel et al., Pharmaceutical Dosage Forms and Drug Delivery Systems, $7^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed-oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 to Lloyd et al. and WO 97/12687 (Eicher et al.).

A representative pharmaceutical composition for use in a nebulizer inhaler comprises an isotonic aqueous solution comprising from about 0.05 μg/mL to about 10 mg/mL of a compound of formula I or a pharmaceutically acceptable salt or solvate or stereoisomer thereof.

In another specific embodiment of this invention, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 μm and about 100 μm and micronized particles of a compound of formula I, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt or solvate or stereoisomer thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company).

A representative pharmaceutical composition for use in a metered-dose inhaler comprises from about 0.01% to about 5% by weight of a compound of formula I, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

For additional examples of processes of preparing respirable particles, and formulations and devices suitable for inhalation dosing see U.S. Pat. No. 6,268,533 to Gao et al., U.S. Pat. No. 5,983,956 to Trofast, U.S. Pat. No. 5,874,063 to Briggner et al., and U.S. Pat. No. 6,221,398 to Jakupovic et al.; and WO 99/55319 (Glaxo Group Ltd.) and WO 00/30614 (AstraZeneca AB).

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipients. For example, a compound of this invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of formula I, or pharmaceutically acceptable salt or solvate or stereoisomer thereof. For example, the pharmaceutical compositions of this invention may further comprise one or more therapeutic agents selected from other bronchodilators (e.g., $PDE_3$ inhibitors, adenosine 2b modulators and $\beta_2$ adrenergic receptor agonists); anti-inflammatory agents (e.g., steroidal anti-inflammatory agents, such as corticosteroids; non-steroidal anti-inflammatory agents (NSAIDs), and $PDE_4$ inhibitors); other muscarinic receptor antagonists (i.e., antichlolinergic agents); antiinfective agents (e.g., Gram positive and Gram negative antibiotics or antivirals); antihistamines; protease inhibitors; and afferent blockers (e.g., $D_2$ agonists and neurokinin modulators). In one particular aspect of the invention, the compound of the invention is co-administered with a $\beta_2$ adrenergic receptor agonist and a steroidal anti-inflammatory agent. The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds disclosed in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds disclosed in WO 02/070490 (Glaxo Group Ltd.); 3-(4-{[6-({(2R)-2-[3-(formylamino)-4-hydroxyphenyl]-2-hydroxyethyl}amino) hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds disclosed in WO 02/076933 (Glaxo Group Ltd.); 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to about 500 µg per dose.

Representative steroidal anti-inflammatory agents that can be used in combination with the compounds of this invention include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl)ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 µg to about 500 µg per dose.

An exemplary combination is a compound of formula I, or pharmaceutically acceptable salt or solvate or stereoisomer thereof, co-administered with salmeterol as the $\beta_2$ adrenergic receptor agonist, and fluticasone propionate as the steroidal anti-inflammatory agent. Another exemplary combination is a compound of formula I, or pharmaceutically acceptable salt or solvate or stereoisomer thereof, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent.

Other suitable combinations include, for example, other anti-inflammatory agents, e.g., NSAIDs (such as sodium cromoglycate; nedocromil sodium; phosphodiesterase (PDE) inhibitors (e.g., theophylline, PDE4 inhibitors or mixed PDE3/PDE4 inhibitors); leukotriene antagonists (e.g., monteleukast); inhibitors of leukotriene synthesis; iNOS inhibitors; protease inhibitors, such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Suitable doses for the other therapeutic agents administered in combination with a compound of the invention are in the range of about 0.05 µg/day to about 100 mg/day.

The following formulations illustrate representative pharmaceutical compositions of the present invention:

FORMULATION EXAMPLE A

A dry powder for administration by inhalation is prepared as follows:

| Ingredients | Amount |
|---|---|
| Compound of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

FORMULATION EXAMPLE B

A dry powder formulation for use in a dry powder inhalation device is prepared as follows:

Representative Procedure: A pharmaceutical composition is prepared having a bulk formulation ratio of micronized compound of the invention to lactose of 1:200. The composition is packed into a dry powder inhalation device capable of delivering between about 10 μg and about 100 μg of the compound of the invention per dose.

FORMULATION EXAMPLE C

A dry powder for administration by inhalation in a metered dose inhaler is prepared as follows:

Representative Procedure: A suspension containing 5 wt % of a compound of the invention and 0.1 wt % lecithin is prepared by dispersing 10 g of the compound of the invention as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

FORMULATION EXAMPLE D

A pharmaceutical composition for use in a metered dose inhaler is prepared as follows:

Representative Procedure: A suspension containing 5 wt % compound of the invention, 0.5 wt % lecithin, and 0.5 wt % trehalose is prepared by dispersing 5 g of active ingredient as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

FORMULATION EXAMPLE E

A pharmaceutical composition for use in a nebulizer inhaler is prepared as follows:

Representative Procedure: An aqueous aerosol formulation for use in a nebulizer is prepared by dissolving 0.1 mg of the compound of the invention in 1 mL of a 0.9% sodium chloride solution acidified with citric acid. The mixture is stirred and sonicated until the active ingredient is dissolved. The pH of the solution is adjusted to a value in the range of from 3 to 8 by the slow addition of NaOH.

FORMULATION EXAMPLE F

Hard gelatin capsules for oral administration are prepared as follows:

| Ingredients | Amount |
|---|---|
| Compound of the invention | 250 mg |
| Lactose (spray-dried) | 200 mg |
| Magnesium stearate | 10 mg |

Representative Procedure: The ingredients are thoroughly blended and then loaded into a hard gelatin capsule (460 mg of composition per capsule).

FORMULATION EXAMPLE G

A suspension for oral administration is prepared as follows:

| Ingredients | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

FORMULATION EXAMPLE H

An injectable formulation is prepared as follows:

| Ingredients | Amount |
|---|---|
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The biphenyl compounds of this invention are expected to be useful as muscarinic receptor antagonists and therefore, such compounds are expected to be useful for treating medical conditions mediated by muscarinic receptors, i.e., medical conditions which are ameliorated by treatment with a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; cardiac arrhythmias, such as sinus bradycardia; Parkinson's disease; cognitive disorders, such as Alzheimer's disease; dismenorrhea; and the like.

In one embodiment, the compounds of this invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome.

When used to treat smooth muscle disorders or other conditions mediated by muscarinic receptors, the compounds of this invention will typically be administered orally, rectally, parenterally or by inhalation in a single daily dose or in multiple doses per day. The amount of active agent administered per dose or the total amount administered per day will typically be determined by the patient's physician and will depend on such factors as the nature and severity of the patients condition, the condition being treated, the age and general health of the patient, the tolerance of the patient to the active agent, the route of administration and the like.

Typically, suitable doses for treating smooth muscle disorders or other disorders mediated by muscarinic receptors will range from about 0.14 μg/kg/day to about 7 mg/kg/day of active agent; including from about 0.15 μg/kg/day to about 5 mg/kg/day. For an average 70 kg human, this would amount to about 10 μg per day to about 500 mg per day of active agent.

In a specific embodiment, the compounds of this invention are useful for treating pulmonary or respiratory disorders, such as COPD or asthma, in mammals including humans. When used to treat such disorders, the compounds of this invention will typically be administered by inhalation in multiple doses per day, in a single daily dose or a single weekly dose. Generally, the dose for treating a pulmonary disorder will range from about 10 μg/day to about 200 μg/day. As used herein, COPD includes chronic obstructive bronchitis and emphysema (see, for example, Barnes, Chronic Obstructive Pulmonary Disease, *N Engl J Med* 343:269-78 (2000)).

When used to treat a pulmonary disorder, the compounds of this invention are optionally administered in combination with other therapeutic agents such as a β$_2$-adrenoreceptor agonist; a corticosteroid, a non-steroidal anti-inflammatory agent, or combinations thereof.

When administered by inhalation, the compounds of this invention typically have the effect of producing bronchodilation. Accordingly, in another of its method aspects, this invention is directed to a method of producing bronchodilation in a patient, the method comprising administering to a patient a bronchodilation-producing amount of a compound of the invention. Generally, the therapeutically effective dose for producing bronchodilation will range from about 10 μg/day to about 200 μg/day.

In another embodiment, the compounds of this invention are used to treat overactive bladder. When used to treat overactive bladder, the compounds of this invention will typically be administered orally in a single daily dose or in multiple doses per day; preferably in a single daily dose. Preferably, the dose for treating overactive bladder will range from about 1.0 to about 500 mg/day.

In yet another embodiment, the compounds of this invention are used to treat irritable bowel syndrome. When used to treat irritable bowel syndrome, the compounds of this invention will typically be administered orally or rectally in a single daily dose or in multiple doses per day. Preferably, the dose for treating irritable bowel syndrome will range from about 1.0 to about 500 mg/day.

Since compounds of this invention are muscarinic receptor antagonists, such compounds are also useful as research tools for investigating or studying biological systems or samples having muscarinic receptors. Such biological systems or samples may comprise $M_1$, $M_2$, $M_3$, $M_4$ and/or $M_5$ muscarinic receptors. Any suitable biological system or sample having muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a muscarinic receptor is contacted with a muscarinic receptor-antagonizing amount of a compound of this invention. The effects of antagonizing the muscarinic receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio) triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.). A compound of this invention will antagonize or decrease the activation of muscarinic receptors in any of the functional assays listed above, or assays of a similar nature. A muscarinic receptor-antagonizing amount of a compound of this invention will typically range from about 0.1 nanomolar to about 100 nanomolar.

Additionally, the compounds of this invention can be used as research tools for discovering new compounds that have muscarinic receptor antagonist activity. In this embodiment, muscarinic receptor binding data (e.g., as determined by in vitro radioligand displacement assays) for a test compound or a group of test compounds is compared to the muscarinic receptor binding data for a compound of this invention to identify those test compounds that have about equal or superior muscarinic receptor binding, if any. This aspect of the invention includes, as separate embodiments, both the generation of comparison data (using the appropriate assays) and the analysis of the test data to identify test compounds of interest.

In another embodiment, the compounds of this invention are used to antagonize a muscarinic receptor in biological system, and a mammal in particular, such as mice, rats, guinea pigs, rabbits, dogs, pigs, humans and so forth. In this embodiment, a therapeutically effective amount of the compound of formula I is administered to the mammal. The effects of antagonizing the muscarinic receptor can then determined using conventional procedures and equipment, examples of which are described above.

Among other properties, compounds of this invention have been found to be potent inhibitors of $M_3$ muscarinic receptor activity. Accordingly, in a specific embodiment, this invention is directed to compounds of formula I having an inhibition dissociation constant ($K_i$) for the $M_3$ receptor subtype of less than or equal to 10 nM; preferably, less than or equal to 5 nM; (as determined, for example, by an in vitro radioligand displacement assay).

Additionally, compounds of this invention have also been found to possess surprising and unexpected duration of action. Accordingly, in another specific embodiment, this invention is directed to compounds of formula I having a duration of action greater than or equal to about 24 hours.

Moreover, compounds of this invention have been found to possess reduced side effects, such as dry mouth, at efficacious doses when administered by inhalation compared to other known muscarinic receptor antagonists administered by inhalation (such as tiotropium).

These properties, as well as the utility of the compounds of this invention, can be demonstrated using various in vitro and in vivo assays well-known to those skilled in the art. For example, representative assays are described in further detail in the following Examples.

EXAMPLES

The following Preparations and Examples illustrate specific embodiments of this invention. In these examples, the following abbreviations have the following meanings:

| | |
|---|---|
| AC | adenylyl cyclase |
| ACh | acetylcholine |
| ACN | acetonitrile |
| BSA | bovine serum albumin |
| cAMP | 3'-5' cyclic adenosine monophosphate |
| CHO | Chinese hamster ovary |
| $cM_5$ | cloned chimpanzee $M_5$ receptor |
| DCM | dichloromethane (i.e., methylene chloride) |
| DIBAL | diisobutylaluminium hydride |
| DIPEA | N,N-diisopropylethylamine |
| dPBS | Dulbecco's phosphate buffered saline |
| DMF | dimethylformamide |
| DMSO | dimethyl sulfoxide |
| EDC | 1-ethyl-3-(3-dimethylaminopropyl)carbodiimide |
| EDCI | 1-(3-dimethylaminopropyl)-3-ethylcarbodiimide hydrochloride |
| EDTA | ethylenediaminetetraacetic acid |
| EtOAc | ethyl acetate |
| EtOH | ethanol |
| FBS | fetal bovine serum |
| FLIPR | fluorometric imaging plate reader |
| HATU | O-(7-azabenzotriazol-1-yl-N, N, N', N'-tetramethyluronium hexafluorophosphate |
| HBSS | Hank's buffered salt solution |
| HEPES | 4-(2-hydroxyethyl)-1-piperazineethanesulfonic acid |
| HOAt | 1-hydroxy-7-azabenzotriazole |
| $hM_1$ | cloned human $M_1$ receptor |
| $hM_2$ | cloned human $M_2$ receptor |
| $hM_3$ | cloned human $M_3$ receptor |
| $hM_4$ | cloned human $M_4$ receptor |
| $hM_5$ | cloned human $M_5$ receptor |
| HOBT | 1-hydroxybenzotriazole hydrate |
| HPLC | high-performance liquid chromatography |
| IPA | isopropanol |
| MCh | methylcholine |
| MTBE | methyl t-butyl ether |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with a Zorbax Bonus RP 2.1×50 mm column (Agilent) having a 3.5 micron particle size. Detection was by UV absorbance at 214 nm. The mobile phases employed were as follows (by volume): A is ACN (2%), water (98%) and TFA (0.1%); and B is ACN (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

Liquid chromatography mass spectrometry (LCMS) data were obtained with an Applied Biosystems (Foster City, Calif.) Model API-150EX instrument. LCMS 10-90 data was obtained using 10 to 90% Mobile Phase B over a 5 minute gradient.

Small-scale purification was conducted using an API 150EX Prep Workstation system from Applied Biosystems. The mobile phases employed were as follows (by volume): A is water and 0.05% TFA; and B is ACN and 0.05% TFA. For arrays (typically about 3 to 50 mg recovered sample size) the following conditions were used: 20 mL/min flow rate; 15 minute gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 minute gradients and a 41.4 mm×250 mm Microsorb BDS column with 10 micron particles (Varian, Palo Alto, Calif.).

Preparation 1

Biphenyl-2-ylcarbamic Acid Piperidin-4-yl Ester

Biphenyl-2-isocyanate (97.5 g, 521 mmol) and 4-hydroxy-N-benzylpiperidine (105 g, 549 mmol) were heated together at 70° C. for 12 hours. The reaction mixture was then cooled to 50° C. and EtOH (1 L) was added and then 6M HCl (191 mL) was added slowly. The resulting mixture was then cooled to ambient temperature and ammonium formate (98.5 g, 1.56 mol) was added and then nitrogen gas was bubbled through the solution vigorously for 20 minutes. Palladium on activated carbon (20 g, 10 wt. % dry basis) was then added and the reaction mixture was heated at 40° C. for 12 hours, and then filtered through a pad of Celite. The solvent was then removed under reduced pressure and 1M HCl (40 mL) was added to the crude residue. The pH of the mixture was then adjusted with 10 N NaOH to pH 12. The aqueous layer was extracted with ethyl acetate (2×150 mL) and the organic layer was dried (magnesium sulfate), filtered and the solvent removed under reduced pressure to give 155 g of the title intermediate (100% yield). HPLC (10-70) $R_t$=2.52; m/z: [M+H$^+$] Calcd for $C_{18}H_{20}N_2O_2$, 297.15. Found, 297.3.

Preparation 2

N-Benzyl-N-methylaminoacetaldehyde

To a 3-necked 2-L flask was added N-benzyl-N-methylethanolamine (30.5 g, 0.182 mol), DCM (0.5 L), DIPEA (95 mL, 0.546 mol) and DMSO (41 mL, 0.728 mol). Using an ice bath, the mixture was cooled to about −10° C. and sulfur trioxide pyridine-complex (87 g, 0.546 mol) was added in 4 portions over 5 minute intervals. The reaction was stirred at −10° C. for 2 hours. Before removing the ice-bath, the reaction was quenched by adding water (0.5 L). The aqueous layer was separated and the organic layer was washed with water (0.5 L) and brine (0.5 L) and then dried over magnesium sulfate and filtered to provide the title compound which was used without further purification.

Preparation 3

Biphenyl-2-ylcarbamic Acid 1-[2-(Benzylmethylamino)ethyl]piperidin-4-yl Ester

To a 2-L flask, containing the product of Preparation 2 in DCM (0.5 L) was added the product of Preparation 1 (30 g, 0.101 mol) followed by sodium triacetoxyborohydride (45 g, 0.202 mol). The reaction mixture was stirred overnight and then quenched by the addition of 1 N hydrochloric acid (0.5 L) with vigorous stirring. Three layers were observed and the aqueous layer was removed. After washing with 1N NaOH (0.5 L), a homogenous organic layer was obtained which was then washed with a saturated solution of aqueous NaCl (0.5 L), dried over magnesium sulfate, filtered and the solvent removed under reduced pressure. The residue was purified by dissolving it in a minimal amount of IPA and cooling this solution to 0° C. to form a solid which was collected and washed with cool IPA to provide 42.6 g of the title compound (95% yield). MS m/z: [M+H$^+$] Calcd for $C_{28}H_{33}N_3O_2$, 444.3. Found, 444.6. $R_f$=3.51 min (10-70 ACN: $H_2O$, reverse phase HPLC).

Preparation 4

Biphenyl-2-ylcarbamic Acid 1-(2-Methylaminoethyl)piperidin-4-yl Ester

To a Parr hydrogenation flask was added the product of Preparation 3 (40 g, 0.09 mol) and EtOH (0.5 L). The flask was flushed with nitrogen gas and palladium on activated carbon (15 g, 10 wt. % (dry basis), 37% wt/wt) was added along with acetic acid (20 mL). The mixture was kept on the Parr hydrogenator under a hydrogen atmosphere (~50 psi) for 3 h. The mixture was then filtered and washed with EtOH. The filtrate was condensed and the residue was dissolved in a minimal amount of DCM. Isopropyl acetate (10 volumes) was added slowly to form a solid which was collected to provide 22.0 g of the title compound (70% yield). MS m/z: [M+H$^+$] Calcd for $C_{21}H_{27}N_3O_2$, 354.2. Found, 354.3. $R_f$=2.96 min (10-70 ACN: $H_2O$, reverse phase HPLC).

Preparation 5

Biphenyl-2-ylcarbamic Acid 1-{2-[(4-Formylbenzoyl)methylamino]ethyl}piperidin-4-yl Ester To a three-necked 1-L flask was added 4-carboxybenzaldehyde (4.77 g, 31.8 mmol), EDC (6.64 g, 34.7 mmol), HOBT (1.91 g, 31.8 mmol), and DCM (200 mL). When the mixture was homogenous, a solution of the product of Preparation 4 (10 g, 31.8 mmol) in DCM (100 mL) was added slowly. The reaction mixture was stirred at room temperature for 16 hours and then washed with water (1×100 mL), 1N HCl (5×60 mL), 1N NaOH (1×100 mL) brine (1×50 mL), dried over sodium sulfate, filtered and concentrated to afford 12.6 g of the title compound (92% yield; 85% purity based on HPLC). MS m/z: [M+H$^+$] Calcd for $C_{29}H_{31}N_3O_4$, 486.2. Found, 486.4. $R_f$=3.12 min (10-70 ACN: $H_2O$, reverse phase HPLC).

Example 1

Biphenyl-2-ylcarbamic Acid 1-(2-{[4-(4-Carbamoylpiperidin-1-ylmethyl)benzoyl]methylamino}ethyl)piperidin-4-yl Ester To a three-necked 2-L flask was added isonipecotamide (5.99 g, 40.0 mmol), acetic acid (2.57 mL), sodium sulfate (6.44 g) and IPA (400 mL). The reaction mixture was cooled to 0-10° C. with an ice bath and a solution of the product of Preparation 5 (11 g, 22.7 mmol) in IPA (300 mL) was slowly added. The reaction mixture was stirred at room temperature for 2 hours and then cooled to 0-10° C. Sodium triacetoxyborohydride (15.16 g, 68.5 mmol) was added portion wise and this mixture was stirred at room temperature for 16 h. The reaction mixture was then concentrated under reduced pressure to a volume of about 50 mL and this mixture was acidified with 1N HCl (200 mL) to pH 3. The resulting mixture was stirred at room temperature for 1 hour and then extracted with DCM (3×250 mL). The aqueous phase was then cooled to 0-5° C. with an ice bath and 50% aqueous NaOH solution was added to adjust the pH of the mixture to 10. This mixture was then extracted with isopropyl acetate (3×300 mL) and the combined organic layers were washed with water (100 mL), brine (2×50 mL), dried over sodium sulfate, filtered and concentrated to afford 10.8 g of the title compound (80% yield. MS m/z: [M+H$^+$] Calcd for $C_{35}H_{43}N_5O_4$, 598.3. Found, 598.6. $R_f$=2.32 min (10-70 ACN: $H_2O$, reverse phase HPLC).

Example 1A

Biphenyl-2-ylcarbamic acid 1-(2-{[4-(4-carbamoylpiperidin-1-ylmethyl)benzoyl]methylamino}ethyl)piperidin-4-yl ester was also prepared as a diphosphate salt using the following procedure:

5.0 g of the product of Example 1 was combined with 80 ml of IPA:ACN (1:1). 4.0 ml of water was added and the mixture heated to 50° C. under stirring, forming a clear solution. To this was added dropwise at 50° C., 16 ml 1M phosphoric acid. The resulting cloudy solution was stirred at 50° C. for 5 hours, then allowed to cool to ambient temperature, under slow stirring, overnight. The resulting crystals were collected by filtration and air-dried for 1 hour, then under vacuum for 18 hours, to give the diphosphate salt of the title compound (5.8 g, 75% yield) as a white crystalline solid (98.3% purity by HPLC).

Example 1B

Biphenyl-2-ylcarbamic acid 1-(2-{[4-(4-carbamoylpiperidin-1-ylmethyl)benzoyl]methylamino}ethyl)piperidin-4-yl ester was also prepared as a monosulfate salt using the following procedure.

442 mg of the product of Example 1 (0.739 mmol of 96% pure material) was taken up in 5 ml of $H_2O$:ACN (1:1) and 1.45 ml of 1N sulfuric acid was added slowly, while monitoring the pH. The pH was adjusted to approx. pH 3.3. The

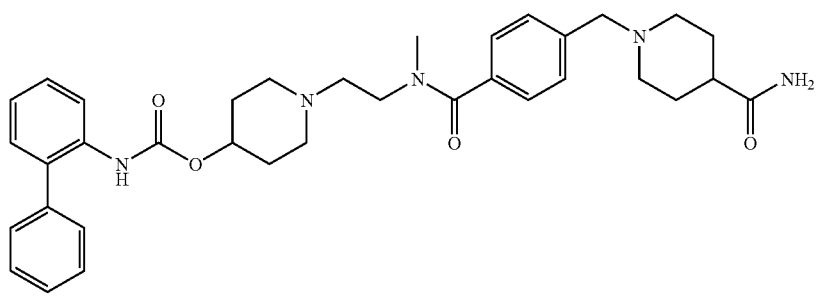

clear solution was filtered through a 0.2 micron filter, frozen and lyophilized to dryness. 161 g of the lyophilized material was dissolved in 8.77 ml of IPA:ACN (10:1). The suspension was heated by placing the vial in a pre-heated 70° C. water bath for 1.5 hours. Oil droplets formed within 5 minutes. The heat was lowered to 60° C. and the mixture heated for an additional 1.5 hours, followed by heating at 50° C. for 40 minutes, at 40° C. for 40 minutes, then at 30° C. for 45 minutes. The heat was turned off and the mixture was allowed to slowly cool to room temperature. The next day, the material was viewed under a microscope and indicated needles and plates. The material was then heated at 40° C. for 2 hours, at 35° C. for 30 minutes, and then at 30° C. for 30 minutes. The heat was turned off and the mixture was allowed to slowly cool to room temperature. The solid was then filtered and dried using a vacuum pump for 1 hour to give the monosulfate salt of the title compound (117 mg, 73% yield).

Example 1C

Biphenyl-2-ylcarbamic acid 1-(2-{[4-(4-carbamoylpiperidin-1-ylmethyl)benzoyl]methylamino}ethyl)piperidin-4-yl ester was also prepared as a dioxalate salt using the following procedure.

510 mg of the product of Example 1 (0.853 mmol of 96% pure material) was taken up in 5 ml of $H_2O$:ACN (1:1) and 1.7 ml of 1M aqueous oxalic acid was added slowly, while monitoring the pH. The pH was adjusted to approx. pH 3.0. The clear solution was filtered through a 0.2 micron filter, frozen and lyophilized to dryness. 150 mg of the lyophilized material was dissolved in 13.1 ml of 94% IPA/6% $H_2O$. The mixture was stirred in a pre-heated 60° C. water bath for 2.5 hours. The heat was turned off and the mixture was allowed to cool to room temperature. The vial was refrigerated at 4° C. After 6 days, an oily material was observed with what appeared to be a crystal on the side of the vial. The vial was then allowed to reach room temperature, at which point seeds (synthesis described below) were added and allowed to sit for 16 days. During this time, more crystals were observed to come out of solution. The solid was then filtered and dried using a vacuum pump for 14 hours to give the dioxalate salt of the title compound (105 mg, 70% yield).

Seed Synthesis 510 mg of the product of Example 1 (0.853 mmol of 96% pure material) was taken up in 5 ml of $H_2O$:ACN (1:1) and 1.7 ml of 1M aqueous oxalic acid was added slowly, while monitoring the pH. The pH was adjusted to approx. pH 3.0. The clear solution was filtered through a 0.2 micron filter, frozen and lyophilized to dryness to yield a dioxalate salt. 31.5 mg of this dioxalate salt was dissolved in 2.76 ml of 94% IPA/6% $H_2O$. The mixture was stirred in a pre-heated 60° C. water bath for 2.5 hours. After 25 minutes, all of the sample was in solution. The heat was turned off and the mixture was allowed to cool to room temperature. The next day, a small amount of viscous material was present. The vial was refrigerated at 4° C. After 4 days, the viscous material was still present. The vial was then placed at room temperature and observed one month later. The material appeared to be solid, and was observed to be crystalline under a microscope. The solid was then filtered and dried using a vacuum pump for 1 hour to give the dioxalate salt (20 mg, 63.5% yield).

Example 1D

Biphenyl-2-ylcarbamic acid 1-(2-{[4-(4-carbamoylpiperidin-1-ylmethyl)benzoyl]methylamino}ethyl)piperidin-4-yl ester was also prepared as a freebase crystal using the following procedure.

230 mg of the product of Example 1 was dissolved in 0.2 ml of $H_2O$:ACN (1:1), using slight heat. The mixture was then heated in a 70° C. water bath for 2 hours. The heat was turned off and the mixture was allowed to cool to room temperature, then refrigerated at 4° C. for 1 hour. 50 µl of water was then added (oiled out), followed by the addition of 40 µl of ACN to get the sample back into solution. Seeds (synthesis described below) were added under slow stirring at room temperature. Crystals started to form, and the mixture was allowed to sit overnight, with slow stirring. The next day, a heat cool cycle was applied (30° C. for 10 minutes, 40° C. for 10 minutes, then 50° C. for 20 minutes). The heat was turned off and the mixture allowed to cool overnight, with slow stirring. The next day, a second heat/cool cycle was applied (60° C. for 1 hour, with dissolving observed at 70° C.). The heat was turned off and the mixture allowed to cool overnight, with slow stirring. The next day, crystals were present and a third heat cool cycle was applied (60° C. for 3 hours). The heat was turned off and the mixture allowed to cool overnight, with slow stirring. The next day, a heat cool cycle was applied (60° C. for 3 hours, slow cool, then 60° C. for 3 hours). The heat was turned off and the mixture allowed to cool overnight, with slow stirring. After 3 days, the solid was filtered and placed on a high vacuum line to remove all solvent and give a freebase crystal of the title compound.

Seed Synthesis 109 mg of the product of Example 1 was dissolved in 0.56 ml of $H_2O$:ACN (1:1). The suspension was left in a vial (cap loosely placed on top) to allow for a slower evaporation time. The vial was placed under a nitrogen flow environment, although the nitrogen was not used for evaporation, only for the environment. A precipitate was visible within 1 day, which was observed to be crystalline under a microscope. The solid was then placed on a high vacuum line to remove all solvent to give the freebase crystal. Quantitative recovery, 97.8% pure by HPLC.

Example 1E

Biphenyl-2-ylcarbamic acid 1-(2-{[4-(4-carbamoylpiperidin-1-ylmethyl)benzoyl]methylamino}ethyl)piperidin-4-yl ester was also prepared as a freebase crystal using the following alternate procedure.

70 mg of the product of Example 1 was dissolved in 0.1 mL ACN. After addition of 0.3 ml MTBE, the solution appeared cloudy. An additional 50 µl of ACN was added to clarify the solution (155 mg/ml ACN:MTBE=1:2). The mixture was left in the vial and capped. A solid appeared by the next day. The solid was then filtered and placed on a high vacuum line to remove all solvent and give a freebase crystal of the title compound.

Example 2

Biphenyl-2-ylcarbamic Acid 1-(2-{[4-(4-Carbamoylpiperidin-1-ylmethyl)-benzoyl]ethylamino}ethyl)piperidin-4-yl Ester

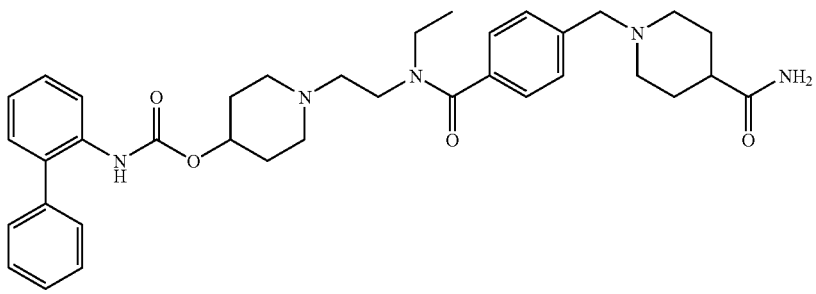

Using the procedure of Example 1, and in Preparation 2 substituting N-benzyl-N-ethylethanolamine in place of N-benzyl-N-methylethanolamine, the title compound was prepared. MS m/z: [M+H$^+$] Calcd for $C_{36}H_{45}N_5O_4$, 612.3. Found, 612.6.

Preparation 6

Biphenyl-2-ylcarbamic Acid 1-(2-{[4-(4-Methyl-esterpiperidin-1-ylmethyl)benzoyl]methylamino}ethyl)piperidin-4-yl Ester

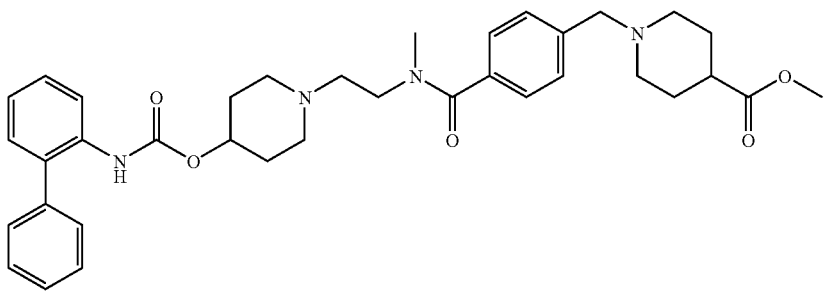

To a three-necked 100 ml flask was added methyl isonipecotate (344 mg, 2.4 mmol), acetic acid (136 μl), sodium sulfate (341 mg) and IPA (20 ml). The reaction mixture was cooled to 0-10° C. with an ice bath and a solution of the product of Preparation 5 (600 mg, 1.24 mmol) in IPA (10 ml) was slowly added. The reaction mixture was stirred at room temperature for 1 hour and then cooled to 0-10° C. Sodium triacetoxyborohydride (763 mg, 3.6 mmol) was added portion wise. After stirring at room temperature for 16 hours, the reaction mixture was then concentrated under reduced pressure to a volume of about 5 ml and diluted with DCM (50 ml). The organic layers were washed with 0.5N HCl (2×30 ml), water (2×30 mL), brine (2×30 ml), dried over sodium sulfate, filtered and concentrated to afford 700 mg of the title compound. (92% yield. MS m/z: [M+H$^+$] Calcd for $C_{36}H_{44}N_4O_5$, 612.8. Found, 613.5.)

Example 3

Biphenyl-2-ylcarbamic Acid 1-(2-{Methyl-[4-(4-methylcarbamoylpiperidin-1-ylmethyl)benzoyl]amino}ethyl)piperidin-4-yl Ester

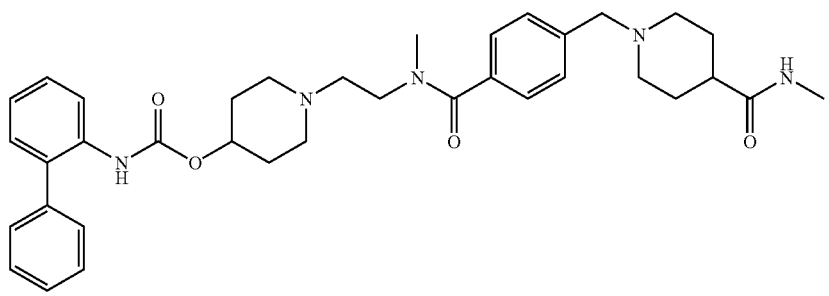

To a 4 ml vial was added the product of Preparation 6 (61.2 mg, 0.1 mmol) and methylamine (1 ml, 2M in MeOH). The reaction mixture was heated at 60° C. for 72 hours and was purified by prep HPLC to afford 46.9 mg of the title compound. (MS m/z: [M+H$^+$] Calcd for $C_{36}H_{45}N_5O_4$, 611.8. Found, 612.4.)

Example 4

Biphenyl-2-ylcarbamic Acid 1-(2-{[4-(4-Ethylcarbamoylpiperidin-1-ylmethyl)benzoyl]methylamino}ethyl)piperidin-4-yl Ester

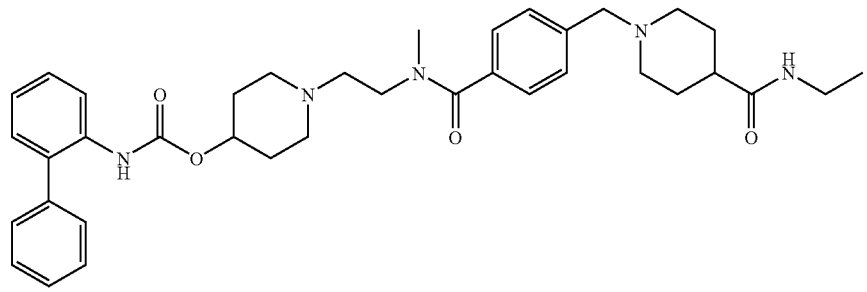

Using the procedure of Example 3, and substituting ethylamine (1 ml, 2M in EtOH) in place of methylamine (1 ml, 2M in MeOH), 17 mg of the title compound was prepared. (MS m/z: [M+H$^+$] Calcd for $C_{37}H_{47}N_5O_4$, 625.8. Found, 626.4.)

Example 5

Biphenyl-2-ylcarbamic Acid 1-(2-{Methyl-[4-(4-propylcarbamoylpiperidin-1-ylmethyl)benzoyl]amino}ethyl)piperidin-4-yl Ester

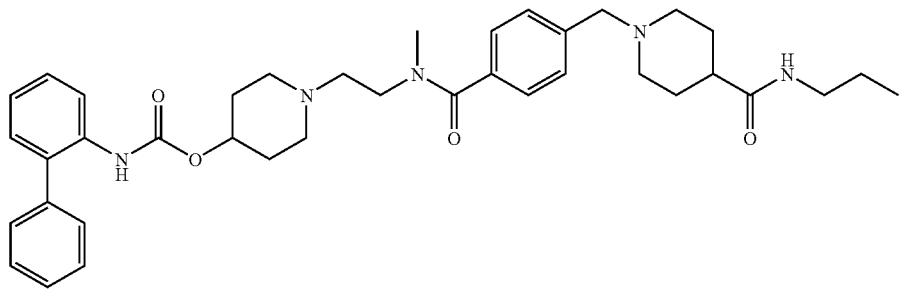

To a 4 ml vial was added the product of Preparation 6 (61.2 mg, 0.1 mmol) and propylamine (1 ml). The reaction mixture was heated at 60° C. for 24 hours and was purified by prep HPLC to afford 39.5 mg of the title compound. (MS m/z: [M+H$^+$] Calcd for $C_{38}H_{49}N_5O_4$, 639.8. Found, 640.4.)

Example 6

Biphenyl-2-ylcarbamic Acid 1-(2-{[4-(4-Isopropylcarbamoylpiperidin-1-ylmethyl)benzoyl]methylamino}ethyl)piperidin-4-yl Ester

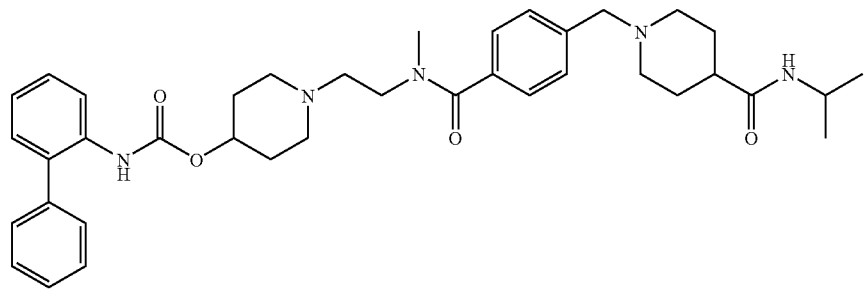

Using the procedure of Example 5, and substituting isopropylamine (1 ml) in place of propylamine (1 ml), 27.8 mg of the title compound was prepared. (MS m/z: [M+H⁺] calcd for $C_{38}H_{49}N_5O_4$, 639.8; found, 640.4.)

Preparation 7

Biphenyl-2-ylcarbamic Acid 1-(2-Boc-aminoethyl)piperidin-4-yl Ester

To a 1-L flask, containing the product of Preparation 1 (25.4 g, 85.6 mmol) in DCM (0.43 L) was added DIPEA (29.9 mL, 171.1 mmol) and 2-(Boc-Amino) ethyl bromide (21.8 g, 94.4 mmol). The reaction was then heated to 50° C. overnight (~18 hours). After overnight, the reaction was then cooled to 0° C. to induce precipitation of the product. The precipitate was filtered and collected to afford the title compound in 42% yield (15.8 g). MS m/z: [M+H⁺] Calcd for $C_{25}H_{33}N_3O_4$, 439.3. Found, 440.4.

Preparation 8

Biphenyl-2-ylcarbamic Acid 1-(2-aminoethyl)piperidin-4-yl Ester

The product of Preparation 7 (3.5 g, 8.1 mmol) was added to 1:1 DCM:TFA (50 mL) and the reaction was allowed to stir at room temperature for 30 minutes. Upon completion, the reaction was diluted with DCM (125 mL) and the mixture was washed with 1N NaOH (200 mL). The organic layer was then washed with water (200 mL), NaCl (sat.) (200 mL), dried over $Na_2SO_4$ and then filtered. The solvent was removed under reduced pressure. The crude material was sufficiently pure to use without further purification. The title compound was obtained in 94% yield (2.6 g, 7.6 mmol). MS m/z: [M+H⁺] Calcd for $C_{20}H_{25}N_3O_2$, 339.2. Found, 339.6.

Preparation 9

2-Fluoro-4-formyl Benzoic Acid

A stirred solution of 4-cyano-2-fluorobenzoic acid (2.5 g, 15.2 mmol) in DCM (100 mL) was cooled to −78° C. and to this was added dropwise DIBAL (30 mL, 45.4 mmol, 25% in toluene), using caution due to $H_2$ evolution. This was allowed to stir at −78° C. for 4 hours. The reaction was quenched via addition of MeOH (10 mL), using caution due to $H_2$ evolution. The organic layer was then washed with 1N HCl (100 mL), water (100 mL), NaCl (sat.) (100 mL), dried over $MgSO_4$ and then filtered. The solvent was removed under reduced pressure. The crude material was sufficiently pure to use without further purification. The title compound was obtained in 78% yield (2.0 g, 11.9 mmol).

Example 7

Biphenyl-2-ylcarbamic Acid 1-{2-[4-(4-Carbamoylpiperidin-1-ylmethyl)-2-fluorobenzoylamino]ethyl}piperidin-4-yl Ester

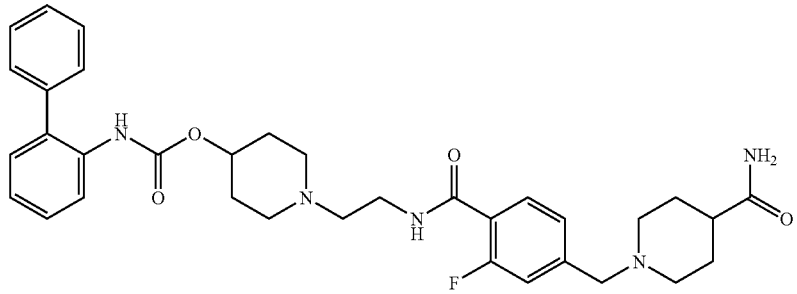

Using the procedure of Example 1 and, in Preparation 5, substituting the product of Preparation 8 in place of the product of Preparation 4 and substituting the product of Preparation 9 in place of 4-carboxybenzaldehyde, the title compound was prepared. MS m/z: [M+H⁺] Calcd for $C_{34}H_{40}FN_5O_4$, 601.7. Found, 602.2.

Example 8

Biphenyl-2-ylcarbamic Acid 1-(2-{[4-(4-Carbamoylpiperidin-1-ylmethyl)-2-fluorobenzoyl]methylamino}ethyl)piperidin-4-yl Ester

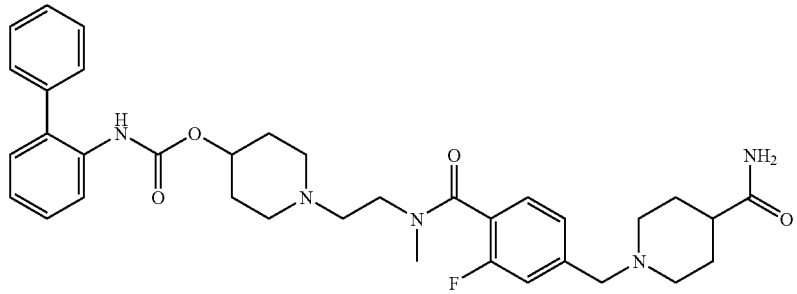

Using the procedure of Example 1 and, in Preparation 5, substituting the product of Preparation 9 in place of 4-carboxybenzaldehyde, the title compound was prepared. MS m/z: [M+H$^+$] Calcd for $C_{35}H_{42}FN_5O_4$, 615.8. Found, 616.2.

Preparation 10

Piperidine-4-carboxylic Acid Diethylamide

To a stirred solution of 1-tert-butoxycarbonylpiperidine-4-carboxylic acid (5 g, 22.0 mmol) in DMF (100 mL) was added diethylamine (4.6 mL, 44 mmol), triethylamine (9.1 mL, 66.0 mmol), HOAt (22.0 mL, 0.5 M in DMF, 22.0 mmol) and finally EDCI (8.4 g, 44 mmol). This was allowed to stir for 14 hours at room temperature. The solvent was then removed under reduced pressure. The mixture was taken up in DCM (100 mL). The organic layer was then washed with water (100 mL), 1N HCl (100 mL), NaCl (sat.) (100 mL), dried over MgSO$_4$ and then filtered. To the organic layer was added TFA (33 mL). The reaction was allowed to stir at room temperature for 2 hours. The solvent was then removed under reduced pressure. The mixture was taken up in DCM (100 mL). The organic layer was then washed with 1N NaOH (100 mL), water (100 mL), NaCl (sat.) (100 mL), dried over MgSO$_4$ and then filtered. The solvent was removed under reduced pressure. The crude material was sufficiently pure to use without further purification. The title compound was obtained in 86% yield (3.5 g, 19.0 mmol).

Example 9

Biphenyl-2-ylcarbamic Acid 1-{2-[4-(4-Diethylcarbamoylpiperidin-1-ylmethyl)-2-fluorobenzoylamino]ethyl}piperidin-4-yl Ester

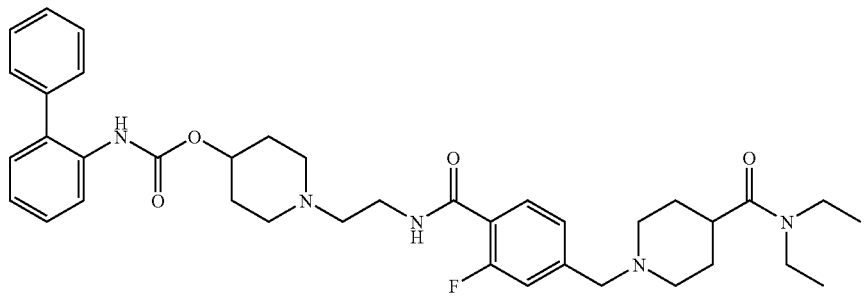

Using the procedure of Example 1 and, in Preparation 5, substituting the product of Preparation 9 in place of 4-carboxybenzaldehyde and substituting the product of Preparation 8 in place of the product of Preparation 4 and, in Example 1, substituting the product of Preparation 10 in place of isonipecotamide, the title compound was prepared. MS m/z: [M+H$^+$] Calcd for $C_{38}H_{48}FN_5O_4$, 657.8. Found, 658.4.

Example 10

Biphenyl-2-ylcarbamic Acid 1-(2-{[4-(4-Diethylcarbamoylpiperidin-1-ylmethyl)-2-fluorobenzoyl]methylamino}ethyl)piperidin-4-yl Ester

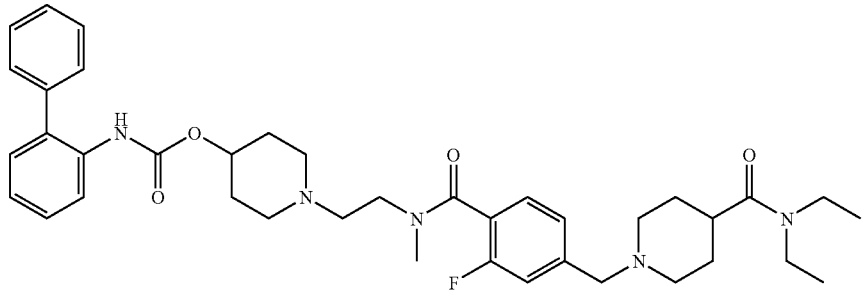

Using the procedure of Example 1 and, in Preparation 5, substituting the product of Preparation 9 in place of 4-carboxybenzaldehyde and, in Example 1, substituting the product of Preparation 10 in place of isonipecotamide the title compound was prepared. MS m/z: [M+H$^+$] Calcd for $C_{39}H_{50}FN_5O_4$, 671.9. Found, 672.4.

Example 11

Biphenyl-2-ylcarbamic Acid 1-(2-{[4-(4-Diethylcarbamoylpiperidin-1-ylmethyl)benzoyl]methylamino}ethyl)piperidin-4-yl Ester

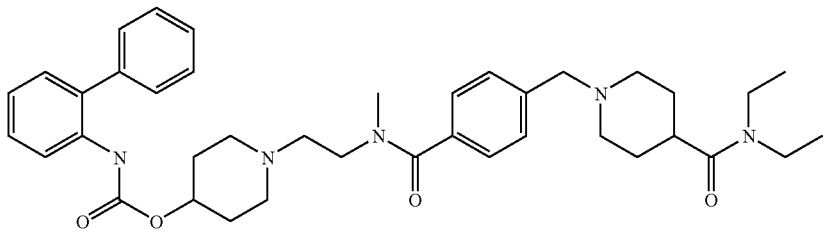

Using the procedure of Example 1 but substituting the product of Preparation 10 in place of isonipecotamide, the title compound was prepared. MS m/z: [M+H$^+$] Calcd for $C_{39}H_{51}N_5O_4$, 653.9. Found, 654.4.

Example 12

Biphenyl-2-ylcarbamic Acid 1-(2-{[4-(3-(S)-Diethylcarbamoylpiperidin-1-ylmethyl)benzoyl]methylamino}ethyl)piperidin-4-yl Ester

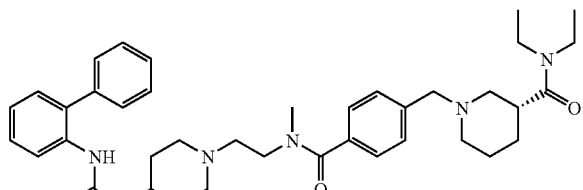

Using the procedure of Example 1 but substituting piperidine-3-(S)-carboxylic acid diethylamide in place of isonipecotamide, the title compound was prepared. MS m/z: [M+H$^+$] Calcd for $C_{39}H_{51}N_5O_4$, 653.9. Found, 654.4.

The preparation of piperidine-3-(S)-carboxylic acid diethylamide was done according to *Chirality* 7(2): 90-95 (1995).

Preparation 11

N-{2-[4-(Biphenyl-2-ylcarbamoyloxy)piperidin-1-yl]ethyl}-2,5-dibromo-N-methylterephthalamic Acid To a 100 mL flask containing the product of Preparation 1 (2.5 g, 7.1 mmol) in DMF (20 mL) was added 2,5-dibromoterephthalic acid (6.88 g, 21.2 mmol) followed by DIPEA (1.6 mL, 9.2 mmol) and HATU (3.23 g, 8.5 mol). The yellow slurry was stirred at room temperature for 3 hours (all material in solution following completion of reaction). The reaction mixture was diluted with DCM (200 mL). To the solution was added 1N NaOH (150 mL) and MeOH (minimal amount added in order to dissolve the fine white precipitate that was observed following the addition of base). The solution was transferred to a separatory funnel and the aqueous layer discarded. The organic layer was washed with 1N HCl (1×150 mL), dried over sodium sulfate, filtered and the solvent removed under reduced pressure to provide 7 g of the title compound (>100% yield due to the presence of residual DMF). This material was used without further purification. MS m/z: [M+H$^+$] Calcd for $C_{29}H_{29}Br_2N_3O_5$, 659.4. Found, 660.3. $R_f$=3.39 min (2-90 ACN: $H_2O$, reverse phase HPLC).

Preparation 12

N-{2-[4-(Biphenyl-2-ylcarbamoyloxy)piperidin-1-yl]ethyl}-2,5-dibromo-N-methylterephthalamic Acid Methyl Ester To a 100 mL flask containing the product of Preparation 11 (7.0 g, 10.6 mmol) was added a solution of toluene/MeOH (9:1, 70 mL). All of the solid material did not dissolve, so an additional 3 mL of MeOH was added. The solution was cooled to 0° C. over an ice bath and trimethylsilyldiazomethane (2.0M solution in hexanes, 6.3 mL, 12.7 mmol) was added via syringe. The reaction mixture was allowed to warm to room temperature. After 2 hours stirring, HPLC and MS analysis indicated that the reaction was not complete. Additional trimethylsilyldiazomethane (10.0 mL) was added and the reaction was stirred at room temperature for 70 hours. Although HPLC analysis had indicated that the reaction was not complete, acetic acid (15 mL) was added to the reaction mixture and the resulting solution was concentrated under reduced pressure. The crude product was purified by silica gel chromatography using a gradient of 2% to 5% MeOH in DCM as the eluent to provide 2.32 g of the title compound (49% yield). MS m/z: [M+H$^+$] calcd for $C_{30}H_{31}Br_2N_3O_5$, 673.4. Found, 674.3. $R_f$=4.26 min (2-90 ACN: $H_2O$, reverse phase HPLC).

Preparation 13

Biphenyl-2-yl-carbamic Acid 1-{2-[(2,5-Dibromo-4-hydroxymethylbenzoyl)methylamino]ethyl}piperidin-4-yl Ester To a 100 mL flask containing the product of Preparation 12 (2.2 g, 3.3 mmol) was added THF (35 mL). Using an ice bath, the mixture was cooled to about 0° C. and lithium aluminum hydride (1.0M solution in THF, 6.6 mL, 6.6 mmol) was added via syringe. The resulting slurry was stirred at room temperature for 4 h. The reaction was quenched by adding 1N NaOH (100 mL). The aqueous layer was separated and the organic layer was washed with brine (50 mL), dried over sodium sulfate, filtered and concentrated under reduced pressure (80.2% pure by HPLC). A portion of the crude product was purified by preparatory HPLC (20-40 ACN: $H_2O$, reverse phase HPLC) to afford 317 mg of the TFA salt. The TFA salt of the desired product was partitioned between EtOAc (10 mL) and saturated sodium bicarbonate solution (10 mL). The organic layer was washed with brine (5 mL), dried over sodium sulfate, filtered and concentrated to provide 223.6 mg of the title compound. MS m/z: [M+H$^+$] Calcd for $C_{29}H_{31}Br_2N_3O_4$, 645.4. Found, 646.3. $R_f$=3.56 min (10-70 ACN: H$_2$O, reverse phase HPLC).

Preparation 14

Methanesulfonic Acid 4-({2-[4-(Biphenyl-2-ylcarbamoyloxy)piperidin-1-yl]ethyl}methylcarbamoyl)-2,5-dibromobenzyl Ester To a 25 mL flask containing the product of Preparation 13 (223.6 mg, 0.346 mmol) was added DCM (10 mL) followed by DIPEA (135.5 uL, 0.778 mmol) and methanesulfonyl chloride (41 uL, 0.528 mmol). The reaction was stirred for 30 minutes at room temperature. To the reaction mixture was then added saturated sodium bicarbonate solution (10 mL). The aqueous layer was discarded and the organic layer was washed with brine (5 mL), dried over sodium sulfate, filtered and concentrated under reduced pressure to afford 229 mg of the title compound (91% yield). MS m/z: [M+H$^+$] Calcd for $C_{30}H_{33}Br_2N_3O_6S$, 723.5. Found, 724.3. $R_f$=3.77 min (10-70 ACN: H$_2$O, reverse phase HPLC).

Example 13

Biphenyl-2-ylcarbamic Acid 1-(2-{[2,5-dibromo-4-(4-carbamoylpiperidin-1-ylmethyl)benzoyl]methylamino}ethyl)piperidin-4-yl Ester

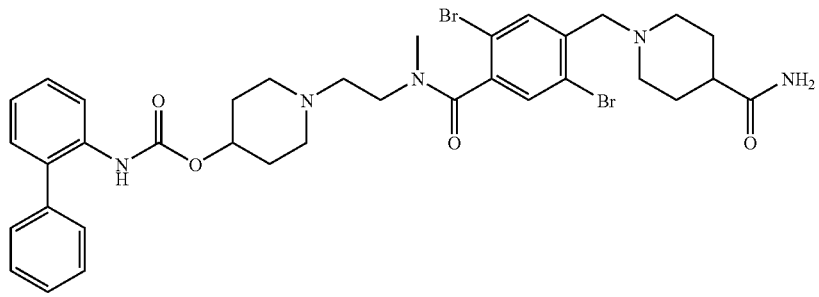

To a 25 mL flask containing the product of Preparation 14 (229 mg, 0.316 mmol) was added isonipecotamide (48.7 mg, 0.380 mmol), DIPEA (110.2 uL, 0.633 mmol), and ACN (4 mL). The reaction mixture was stirred at room temperature for 63 hours under a nitrogen atmosphere. The reaction mixture was then diluted with DCM (15 mL) and washed with saturated aqueous sodium bicarbonate solution. The product was extracted into the aqueous layer using 1.0 N HCl (2×10 mL). The aqueous layer was washed with DCM (2×15 mL) and the pH was adjusted to 10-11 using 1.0 N NaOH. This mixture was then extracted with DCM (3×20 mL) and the combined organic layers were washed with brine (10 mL), dried over sodium sulfate, filtered and concentrated to provide the title compound. MS m/z: [M+H$^+$] Calcd for $C_{35}H_{41}Br_2N_5O_4$, 756.5. Found, 756.3; $R_f$=2.65 min (10-70 ACN: H$_2$O, reverse phase HPLC).

Example 14

Biphenyl-2-yl-carbamic Acid 1-(2-{[4-(2-Carbamoyl-piperidin-1-ylmethyl)benzoyl]methylamino}ethyl)piperidin-4-yl Ester

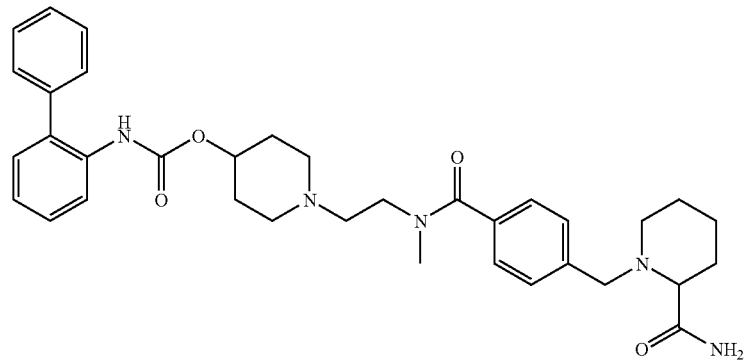

The title compound was prepared using the procedures described in Example 1, and substituting the appropriate starting materials. MS m/z: [M+H$^+$] Calcd for $C_{35}H_{43}N_5O_4$, 598.3. Found, 597.8.

Example 15

Biphenyl-2-yl-carbamic Acid 1-(2-{[4-(4-Carbamoyl-piperidin-1-ylmethyl)-2-methoxybenzoyl]methylamino}ethyl)piperidin-4-yl Ester

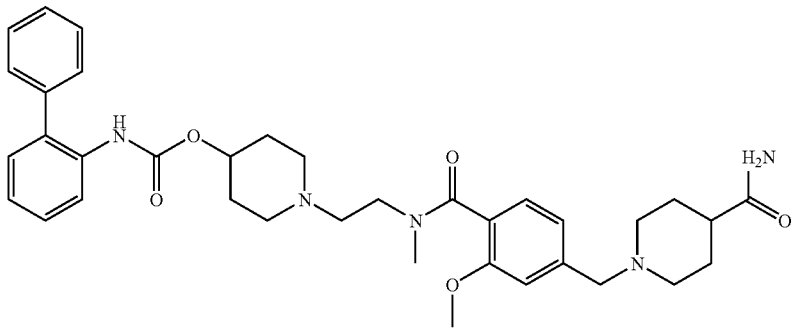

To a stirred solution of 4-bromo-3-methoxy-benzoic acid (15.0 g, 58 mmol) in DMSO (150 mL) was added NaHCO$_3$ (20.0 g, 230 mmol). This was heated to 80° C. for 18 hours. The reaction was then cooled to room temperature and the solvent removed under reduced pressure. The crude reaction mixture was then dissolved in DCM (200 mL) and washed with 1N HCl (100 mL), water (100 mL), NaCl (sat.) (100 mL), dried over MgSO$_4$ and then filtered. The solvent was removed under reduced pressure. The crude material was sufficiently pure to use without further purification. The product, 4-formyl-3-methoxybenzoic acid methyl ester, was obtained in 79% yield (8.9 g, 45.8 mmol).

To a stirred solution of 4-formyl-3-methoxy-benzoic acid methyl ester (5.0 g, 26 mmol) in tert-butyl alcohol (200 mL) was added NaH$_2$PO$_4$-2H$_2$O (3.6 g, 26 mmol), water (50 mL), 2-methyl-2-butene (11 mL, 104 mmol), and finally NaClO$_2$ (7.02 g, 78 mmol). The reaction was allowed to stir at room temperature for 4 hours. The solvent was then removed under reduced pressure. The crude reaction mixture was then dissolved in DCM (200 mL) and the product was extracted with 1N NaOH (200 mL). The aqueous layer was washed with DCM (200 mL) and then neutralized with 6N HCl (~40 mL) and the product extracted with DCM (200 mL). The organic layer was then washed with water (100 mL), NaCl (sat.) (100 mL), dried over MgSO$_4$ and then filtered. The solvent was removed under reduced pressure. The crude material was sufficiently pure to use without further purification. The product, 2-methoxyterephthalic acid 4-methyl ester, was obtained in 47% yield (2.4 g, 12.3 mmol).

To a stirred solution of 2-methoxyterephthalic acid 4-methyl ester (450 mg, 2.1 mmol) in DMF (10 mL) was added EDC (630 mg, 3.3 mmol), HOAt (2.4 mL, 1.18 mmol, 0.5M in DMF) and DIPEA (1.3 mL, 7.05 mmol). When the mixture was homogenous, a solution of the product of Preparation 4 (830 mg, 2.4 mmol) was added slowly. The reaction mixture was stirred at room temperature for 16 hours and then washed with water (100 mL), 1N HCl (100 mL), 1N NaOH (100 mL), brine (100 mL), dried over MgSO$_4$, filtered and concentrated to afford an ester product in 89% yield (1.04 g, 1.9 mmol). MS m/z: [M+H$^+$] Calcd for $C_{31}H_{35}N_3O_6$, 545.6. Found, 546.6.

To a stirred solution of this ester product (1.0 g, 1.8 mmol) in THF (100 mL) at 0° C., was added methanol (57 μL, 1.8 mmol), followed by LiAlH$_4$ (1.8 mL, 1.8 mmol, 1.0M in THF) was added. The ice bath was removed, and the reaction mixture was stirred at room temperature for 1 hour. The reaction was quenched with 1N HCl (aq) at 0° C. until no more bubbling, stirring was continued for 10 minutes. The solvent was removed under reduced pressure. The crude reaction mixture was taken up in DCM (100 mL) and washed with water (100 mL), NaCl (sat.) (100 mL), dried over MgSO$_4$ and then filtered. The solvent was removed under reduced pressure. The crude material was sufficiently pure to use without further purification. The alcohol product was obtained in 89% yield (831 mg, 1.6 mmol). MS m/z: [M+H$^+$] Calcd for $C_{30}H_{35}N_3O_5$, 517.6. Found, 518.6.

To a stirred solution of this alcohol product (78 mg, 1.5 mmol) in DCM (2.5 mL) at −15° C. was added DMSO (130 μL, 22.5 mmol), DIPEA (130 μL, 7.5 mmol). To the solution was added sulfur trioxide-pyridine complex (240 mg, 15 mmol). After 30 minutes, the reaction mixture was quenched with H$_2$O (~3 mL). Two layers were separated, the organic layer was dried over MgSO$_4$, filtered and the aldehyde product was used directly in the next reaction.

Using the procedure of Example 1 but substituting this aldehyde product in place of the product of Preparation 5, the title compound was prepared. MS m/z: [M+H$^+$] Calcd for $C_{36}H_{45}N_5O_5$, 627.3. Found, 628.2.

Using the procedures described herein and substituting the appropriate starting materials, the following compounds were prepared:

Example 16

Biphenyl-2-yl-carbamic acid 1-(2-{[5-(4-carbamoylpiperidin-1-ylmethyl)thiophene-2-carbonyl]methylamino}ethyl)piperidin-4-yl ester. MS m/z: [M+H$^+$] Calcd for $C_{33}H_{41}N_5O_4S$, 604.3. Found 604.2.

Example 17

Biphenyl-2-yl-carbamic acid 1-(2-{[5-((R)-3-diethylcarbamoylpiperidin-1-ylmethyl)thiophene-2-carbonyl]methylamino}ethyl)piperidin-4-yl ester. MS m/z: [M+H$^+$] Calcd for $C_{37}H_{49}N_5O_4S$, 660.4. Found 660.4.

Example 18

Biphenyl-2-yl-carbamic acid 1-(2-{[5-((R)-3-diethylcarbamoylpiperidin-1-ylmethyl)thiophene-2-carbonyl]amino}ethyl)piperidin-4-yl ester. MS m/z: [M+H$^+$] Calcd for $C_{36}H_{47}N_5O_4S$, 646.3. Found 646.4.

Example 19

Biphenyl-2-yl-carbamic acid 1-(2-{[5-(4-cabamoylpiperidin-1-ylmethyl)thiophene-2-carbonyl]amino}ethyl)piperidin-4-yl ester. MS m/z: [M+H$^+$] Calcd for $C_{32}H_{39}N_5O_4S$, 590.3. Found 590.2.

Example 20 biphenyl-2-yl-carbamic acid 1-(2-{[5-((R)-3-diethylcarbamoyl piperidin-1-ylmethyl)-1H-pyrrole-2-carbonyl]methylamino}ethyl)piperidin-4-yl ester. MS m/z: [M+H$^+$] Calcd for $C_{37}H_{50}N_6O_4$, 643.4. Found 643.2.

Example 21

Biphenyl-2-yl-carbamic acid 1-(2-{[5-(4-carbamoylpiperidin-1-ylmethyl)-1H-pyrrole-2-carbonyl]methylamino}ethyl)piperidin-4-yl ester. MS m/z: [M+H$^+$] Calcd for $C_{33}H_{42}N_6O_4$, 587.3. Found 587.2.

Example 22

Biphenyl-2-yl-carbamic acid 1-(2-{[5-((R)-3-diethylcarbamoyl piperidin-1-ylmethyl)furan-2-carbonyl]methylamino}ethyl)piperidin-4-yl ester. MS m/z: [M+H$^+$] Calcd for $C_{37}H_{49}N_5O_5$, 644.4. Found 644.4.

Example 23

Biphenyl-2-yl-carbamic acid 1-(2-{[5-(4-diethylcarbamoyl-piperidin-1-ylmethyl)furan-2-carbonyl]methylamino}ethyl)piperidin-4-yl ester. MS m/z: [M+H$^+$] Calcd for $C_{37}H_{49}N_5O_5$, 644.4. Found 644.4.

Example 24

Biphenyl-2-yl-carbamic acid 1-(2-{[5-(4-carbamoylpiperidin-1-ylmethyl)furan-2-carbonyl]-amino}ethyl)piperidin-4-yl ester. MS m/z: [M+H$^+$] Calcd for $C_{32}H_{39}N_5O_5$, 574.3. Found 574.2.

Example 25

Biphenyl-2-yl-carbamic acid 1-(2-{[5-((R)-3-diethylcarbamoyl piperidin-1-ylmethyl)furan-2-carbonyl]amino}ethyl)piperidin-4-yl ester. MS m/z: [M+H$^+$] Calcd for $C_{36}H_{47}N_5O_5$, 630.4.

Example 26

Biphenyl-2-yl-carbamic acid 1-[2-({3-[4-(3-carbamoylpiperidin-1-ylmethyl)phenyl]propionyl}methylamino)ethyl]piperidin-4-yl ester. MS m/z: [M+H$^+$] calcd for $C_{37}H_{47}N_5O_4$, 626.4; Found 625.8.

Example 27

Biphenyl-2-yl-carbamic acid 1-[2-({3-[4-(4-carbamoylpiperidin-1-ylmethyl)phenyl]propionyl}methylamino)ethyl]piperidin-4-yl ester. MS m/z: [M+H$^+$] calcd for $C_{37}H_{47}N_5O_4$, 626.4; Found 625.8.

Example 28

Biphenyl-2-yl-carbamic acid 1-(2-{3-[4-(4-carbamoylpiperidin-1-ylmethyl)phenyl]propionylamino}ethyl)piperidin-4-yl ester. MS m/z: [M+H$^+$] Calcd for $C_{36}H_{45}N_5O_4$, 612.4. Found 611.8.

Example 29

Biphenyl-2-yl-carbamic acid 1-(2-{3-[4-(4-diethylcarbamoyl piperidin-1-ylmethyl)phenyl]propionylamino}ethyl)piperidin-4-yl ester. MS m/z: [M+H$^+$] Calcd for $C_{40}H_{53}N_5O_4$, 668.4. Found 667.9.

Example 30

Biphenyl-2-yl-carbamic acid 1-(2-{3-[4-(3-diethylcarbamoyl piperidin-1-ylmethyl)phenyl]propionylamino}ethyl)piperidin-4-yl ester. MS m/z: [M+H$^+$] Calcd for $C_{40}H_{53}N_5O_4$, 668.4. Found 667.9.

Using the procedures described herein and substituting the appropriate starting materials, the following compounds can be prepared:

Example 31

Biphenyl-2-ylcarbamic acid 1-{2-[4-(4-carbamoyl-piperidin-1-ylmethyl)benzoylamino]ethyl}piperidin-4-yl ester;

Example 32

Biphenyl-2-ylcarbamic acid 1-(2-{[4-(4-carbamoylpiperidin-1-ylmethyl)-2-chloro-benzoyl]methylamino}ethyl)piperidin-4-yl ester;

Example 33

Biphenyl-2-ylcarbamic acid 1-(2-{[4-(4-carbamoylpiperidin-1-ylmethyl)-2-chloro-5-methoxybenzoyl]methylamino}ethyl)piperidin-4-yl ester; and

Example 34

Biphenyl-2-ylcarbamic acid 1-[2-({2-[4-(4-carbamoylpiperidin-1-ylmethyl)phenyl]acetyl}methylamino)ethyl]piperidin-4-yl ester.

Assay 1

Radioligand Binding Assay

A. Membrane Preparation from Cells Expressing hM$_1$, hM$_2$, hM$_3$ and hM$_4$ Muscarinic Receptor Subtypes CHO cell lines stably expressing cloned human hM$_1$, hM$_2$, hM$_3$ and hM$_4$ muscarinic receptor subtypes, respectively, were grown to near confluency in medium consisting of HAM's F-12 supplemented with 10% FBS and 250 µg/mL Geneticin. The cells were grown in a 5% CO$_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared hM$_5$ receptor membranes were purchased directly from Perkin Elmer and stored at −80° C. until use.

B. Radioligand Binding Assay on Muscarinic Receptor Subtypes $hM_1$, $hM_2$, $hM_3$, $hM_4$ and $hM_5$ Radioligand binding assays were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$. The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. For example, the compounds of Examples 1 and 2 were found to have a $K_i$ value of less than about 5 nM for the $M_3$ muscarinic receptor subtype in this assay.

Assay 2

Muscarinic Receptor Functional Potency Assays

A. Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor.

cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6$-$2.8 \times 10^6$ cells/mL.

The test compound was initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine was diluted in a similar manner.

To measure oxotremorine inhibition of AC activity, 25 μL forskolin (25 μM final concentration diluted in dPBS), 25 μL diluted oxotremorine, and 50 μL cells were added to agonist assay wells. To measure the ability of a test compound to block oxotremorine-inhibited AC activity, 25 μL forskolin and oxotremorine (25 μM and 5 μM final concentrations, respectively, diluted in dPBS), 25 μL diluted test compound, and 50 μL cells were added to remaining assay wells.

Reactions were incubated for 10 minutes at 37° C. and stopped by addition of 100 μL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher functional activity at the receptor tested. Exemplary compounds of the invention that were tested in this assay, typically were found to have a $K_i$ value of less than about 10 nM for blockade of oxotremorine-inhibition of forskolin-mediated cAMP accumulation in CHO-K1 cells expressing the $hM_2$ receptor. For example, the compound of Example 1 was found to have a $K_i$ value of less than about 5 nM.

B. Blockade of Agonist-Mediated [$^{35}$S]GTPγS-Binding

In a second functional assay, the functional potency of test compounds can be determined by measuring the ability of the compounds to block oxotremorine-stimulated [$^{35}$S]GTPγS-binding in CHO-K1 cells expressing the $hM_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL of assay buffer with [$^{35}$S]GTPγS (0.4 nM), 25 μL of oxotremorine($EC_{90}$) and GDP (3 μM), 25 μL of diluted test compound and 25 μL CHO cell membranes expressing the hM$_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. Exemplary compounds of the invention that were tested in this assay, typically were found to have a $K_i$ value of less than about 10 nM for blockade of oxotremorine-stimulated [$^{35}$S] GTPγS-binding in CHO-K1 cells expressing the hM$_2$ receptor. For example, the compound of Example 1 was found to have a $K_i$ value of less than about 5 nM.

C. Blockade of Agonist-Mediated Calcium Release Via FLIPR Assays

Muscarinic receptor subtypes (M$_1$, M$_3$ and M$_5$ receptors), which couple to G$_q$ proteins, activate the phospholipase C (PLC) pathway upon agonist binding to the receptor. As a result, activated PLC hydrolyzes phosphatyl inositol diphosphate (PIP$_2$) to diacylglycerol (DAG) and phosphatidyl-1,4,5-triphosphate (IP$_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human M$_1$ and M$_3$, and chimpanzee M$_5$ receptors. Antagonist potency can be determined by the ability of antagonists to inhibit agonist-mediated increases in intracellular calcium.

For FLIPR calcium stimulation assays, CHO cells stably expressing the hM$_1$, hM$_3$ and cM$_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leaving 50 μL/well of FLIPR buffer. The cells are then incubated with 50 μL/well of 4 μM FLUO-4AM (a 2× solution was made) for 40 minutes at 37° C., 5% carbon dioxide. Following the dye incubation period, cells are washed two times with FLIPR buffer, leaving a final volume of 50 μL/well.

To determine antagonist potency, the dose-dependent stimulation of intracellular Ca$^{2+}$ release for oxotremorine is first determined so that antagonist potency can later be measured against oxotremorine stimulation at an EC$_{90}$ concentration. Cells are first incubated with compound dilution buffer for 20 minutes, followed by agonist addition, which is performed by the FLIPR. An EC$_{90}$ value for oxotremorine is generated according to the method detailed in the FLIPR measurement and data reduction section below, in conjunction with the formula $EC_F = ((F/100-F)^{\wedge}1/H)*EC_{50}$. An oxotremorine concentration of $3 \times EC_F$ is prepared in stimulation plates such that an EC$_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine EC$_{50}$ value as the $K_D$ and the oxotremorine EC$_{90}$ for the ligand concentration according to the Cheng-Prusoff equation (Cheng & Prusoff, 1973).

In this assay, a lower $K_i$ value indicates that the test compound has a higher functional activity at the receptor tested. Exemplary compounds of the invention that were tested in this assay, typically were found to have a $K_i$ value of less than about 10 nM for blockade of agonist-mediated calcium release in CHO cells stably expressing the hM$_3$ receptor. For example, the compound of Example 1 was found to have a $K_i$ value of less than about 5 nM for the hM$_3$ receptor.

Assay 3

Determination of Duration of Bronchoprotection in Guinea Pig Model of Acetylcholine-Induced Bronchoconstriction This in vivo assay was used to assess the bronchoprotective effects of test compounds exhibiting muscarinic receptor antagonist activity.

Groups of six male guinea pigs (Duncan-Hartley (HsdPoc: DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). These aerosols were generated from aqueous solutions using an LC Star Nebulizer Set (Model 22F51, PARI Respiratory Equipment, Inc. Midlothian, Va.) driven by a mixture of gases (CO$_2$=5%, O$_2$=21% and N$_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre- and post-nebulization weights of the filled nebulizer.

The bronchoprotective effects of test compounds administered via inhalation were evaluated using whole body plethysmography at 1.5, 24, 48 and 72 hours post-dose.

Forty-five minutes prior to the start of the pulmonary evaluation, each guinea pig was anesthetized with an intramuscular injection of ketamine (43.75 mg/kg), xylazine (3.50 mg/kg)

and acepromazine (1.05 mg/kg). After the surgical site was shaved and cleaned with 70% alcohol, a 2-3 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic mixture. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values were within the range 0.3-0.9 mL/cm H$_2$O for compliance and within the range 0.1-0.199 cm H$_2$O/mL per second for resistance, the pulmonary evaluation was initiated. A Buxco pulmonary measurement computer program enabled the collection and derivation of pulmonary values.

Starting this program initiated the experimental protocol and data collection. The changes in volume over time that occur within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with ACh. ACh (0.1 mg/mL) was infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance had not returned to baseline values at 3 minutes following each ACh dose, the guinea pig's lungs were inflated 3 times with 4 mL of air from a 10 mL calibration syringe. Recorded pulmonary parameters included respiration frequency (breaths/minute), compliance (mL/cm H$_2$O) and pulmonary resistance (cm H$_2$O/mL per second). Once the pulmonary function measurements were completed at minute 35 of this protocol, the guinea pig was removed from the plethysmograph and euthanized by carbon dioxide asphyxiation.

The data were evaluated in one or both of the following ways:

(a) Pulmonary resistance (R$_L$, cm H$_2$O/mL per second) was calculated from the ratio of "change in pressure" to "the change in flow." The R$_L$ response to ACh (60 µg/min, IH) was computed for the vehicle and the test compound groups. The mean ACh response in vehicle-treated animals, at each pre-treatment time, was calculated and used to compute % inhibition of ACh response, at the corresponding pre-treatment time, at each test compound dose. Inhibition dose-response curves for 'R$_L$' were fitted with a four parameter logistic equation using GraphPad Prism, version 3.00 for Windows (GraphPad Software, San Diego, Calif.) to estimate bronchoprotective ID$_{50}$ (dose required to inhibit the ACh (60 µg/min) bronchoconstrictor response by 50%). The equation used was as follows:

$$Y = \text{Min} + (\text{Max} - \text{Min})/(1 + 10^{((\log ID50 - X)*Hillslope)})$$

where X is the logarithm of dose, Y is the response (% Inhibition of ACh induced increase in R$_L$). Y starts at Min and approaches asymptotically to Max with a sigmoidal shape.

(b) The quantity PD$_2$, which is defined as the amount of ACh or histamine needed to cause a doubling of the baseline pulmonary resistance, was calculated using the pulmonary resistance values derived from the flow and the pressure over a range of ACh or histamine challenges using the following equation (which is derived from a equation used to calculate PC$_{20}$ values described in American Thoracic Society. Guidelines for methacholine and exercise challenge testing—1999. *Am J Respir Crit Care Med.* 161: 309-329 (2000)):

$$PD_2 = \text{antilog}\left[\log C_1 + \frac{(\log C_2 - \log C_1)(2R_0 - R_1)}{R_2 - R_1}\right]$$

where:
  C$_1$=concentration of ACh or histamine preceding C$_2$
  C$_2$=concentration of ACh or histamine resulting in at least a 2-fold increase in pulmonary resistance (R$_L$)
  R$_0$=Baseline R$_L$ value
  R$_1$=R$_L$ value after C$_1$
  R$_2$=R$_L$ value after C$_2$ An efficacious dose was defined as a dose that limited the bronchorestriction response to a 50 µg/mL dose of ACh to a doubling of the baseline pulmonary resistance (PD$_{2(50)}$).

Statistical analysis of the data was performed using a two-tailed Students t-test. A P-value <0.05 was considered significant.

Generally, test compounds having a PD$_{2(50)}$ less than about 200 µg/mL for ACh-induced bronchoconstriction at 1.5 hours post-dose in this assay are preferred. For example, the compound of Example 1 was found to have a PD$_{2(50)}$ less than about 200 µg/mL for ACh-induced bronchoconstriction at 1.5 hours post-dose.

Assay 4

Inhalation Guinea Pig Salivation Assay

Guinea pigs (Charles River, Wilmington, Mass.) weighing 200-350 g were acclimated to the in-house guinea pig colony for at least 3 days following arrival. Test compound or vehicle were dosed via inhalation (IH) over a 10 minute time period in a pie shaped dosing chamber (R&S Molds, San Carlos, Calif.). Test solutions were dissolved in sterile water and delivered using a nebulizer filled with 5.0 mL of dosing solution. Guinea pigs were restrained in the inhalation chamber for 30 minutes. During this time, guinea pigs were restricted to an area of approximately 110 sq. cm. This space was adequate for the animals to turn freely, reposition themselves, and allow for grooming. Following 20 minutes of acclimation, guinea pigs were exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs were evaluated at 1.5, 6, 12, 24, 48, or 72 hrs after treatment.

Guinea pigs were anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals were placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) was inserted in the guinea pig's mouth. Five minutes later, the muscarinic agonist pilocarpine (3.0 mg/kg, SC) was administered and the gauze pad was immediately discarded and replaced by a new pre-weighed gauze pad. Saliva was collected for 10 minutes, at which point the gauze pad was weighed and the difference in weight recorded to determine the amount of accumulated saliva (in mg). The mean amount of saliva collected for animals receiving the vehicle and each dose of test compound was calculated. The vehicle group mean was considered to be 100% salivation. Results were calculated using result means (n=3 or greater). Confidence intervals (95%) were calculated for each dose at each time point using two-way ANOVA. This model is a modified version of the procedure described in Rechter, "Estimation of anticholinergic drug effects in mice by antagonism against pilocarpine-induced salivation" Ata Pharmacol Toxicol 24:243-254 (1996).

The mean weight of saliva in vehicle-treated animals, at each pre-treatment time, was calculated and used to compute % inhibition of salivation, at the corresponding pre-treatment time, at each dose. The inhibition dose-response data were fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used was as follows:

$$Y=\text{Min}+(\text{Max}-\text{Min})/(1+10^{((\log ID50-X)*Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ was used to compute the apparent lung selectivity index of the test compound. Generally, compounds having an apparent lung selectivity index greater than about 5 are preferred. For example, in this assay, the compound of Example 1 had an apparent lung-selectivity index greater than about 5.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g were used in these studies. Under isoflurane anesthesia (to effect), animals were instrumented with common carotid artery and jugular vein catheters (PE-50 tubing). The catheters were exteriorized utilizing a subcutaneous tunnel to the subscapular area. All surgical incisions were sutured with 4-0 Ethicon Silk and the catheters locked with heparin (1000 units/mL). Each animal was administered saline (3 mL, SC) at the end of surgery as well as buprenorphine (0.05 mg/kg, IM). Animals were allowed to recover on a heating pad before being returned to their holding rooms.

Approximately 18 to 20 hours following surgery, the animals were weighed and the carotid artery catheter on each animal was connected to a transducer for recording arterial pressure. Arterial pressure and heart rate was recorded using a Biopac MP-100 Acquisition System. Animals were allowed to acclimate and stabilize for a period of 20 minutes.

Each animal was challenged with MCh (0.3 mg/kg, IV) administered through the jugular venous line and the cardiovascular response was monitored for 10 minutes. The animals were then placed into the whole body dosing chamber, which was connected to a nebulizer containing the test compound or vehicle solution. The solution was nebulized for 10 minutes using a gas mixture of breathable air and 5% carbon dioxide with a flow rate of 3 liters/minute. The animals were then removed from the whole body chamber and returned to their respective cages. At 1.5 and 24 hours post-dosing, the animals were re-challenged with MCh (0.3 mg/kg, IV) and the hemodynamic response was determined. Thereafter, the animals were euthanized with sodium pentobarbital (150 mg/kg, IV).

MCh produces a decrease in mean arterial pressure (MAP) and decrease in heart rate (bradycardia). The peak decrease, from baseline, in MAP (depressor responses) was measured for each MCh challenge (before and after IH dosing). The bradycardic effects were not used for analysis since these responses were not robust and reproducible. The effects of treatment on the MCh responses are expressed as % inhibition (mean +/−SEM) of the control depressor responses. Two-way ANOVA with the appropriate post-hoc test was used to test the effects of treatment and pre-treatment time. The depressor responses to MCh were relatively unchanged at 1.5 and 24 hours after inhalation dosing with vehicle.

The ratio of the anti-depressor $ID_{50}$ to bronchoprotective $ID_{50}$ was used to compute apparent lung-selectivity of the test compound. Generally, compounds having an apparent lung-selectivity index greater than 5 are preferred. For example, in this assay, the compound of Example 1 had an apparent lung-selectivity index greater than 5.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A pharmaceutical composition comprising a pharmaceutically acceptable carrier and a therapeutically effective amount of a compound having the formula:

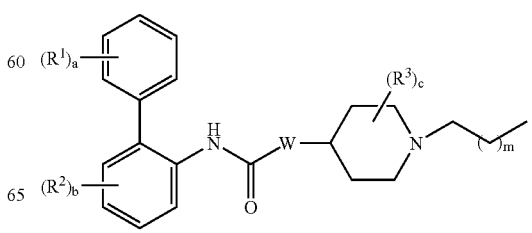

-continued

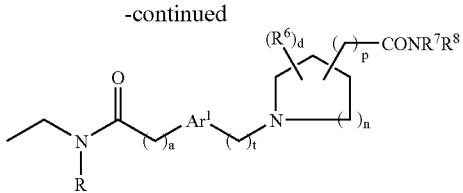

wherein:
a is 0 or 1;
$R^1$ is halo;
b is 0 or 1;
$R^2$ is halo;
m is 0 or 1;
$R^4$ is selected from hydrogen and (1-4C)alkyl;
s is 0, 1 or 2;
$Ar^1$ represents a phenylene group substituted with $(R^5)_q$ where q is 0 or an integer from 1 to 4 and each $R^5$ is independently selected from halo, hydroxy, (1-4C)alkyl, and (1-4C)alkoxy;
t is 0, 1 or 2;
n is 0 or an integer from 1 to 3;
p is 0 or 1; and
$R^7$ and $R^8$ are independently hydrogen or (1-4C)alkyl;
wherein each alkyl group in $R^5$, $R^7$, and $R^8$ is optionally substituted with 1 to 5 fluoro substituents;
or a pharmaceutically acceptable salt or stereoisomer thereof.

2. The pharmaceutical composition of claim 1, wherein m is 0, s is 0 and t is 1.

3. The pharmaceutical composition of claim 1, wherein $Ar^1$ represents phen-1,3-ylene or phen-1,4-ylene, optionally substituted with one or two $R^5$ substituents.

4. The pharmaceutical composition of claim 1, wherein $R^4$ is selected from hydrogen, methyl and ethyl.

5. The pharmaceutical composition of claim 1, wherein $R^7$ is selected from hydrogen, methyl, ethyl, n-propyl and isopropyl; and $R^8$ is hydrogen.

6. The pharmaceutical composition of claim 1, wherein $R^7$ and $R^8$ are ethyl.

7. The pharmaceutical composition of claim 1, wherein a and b each represent 0; m is 0; s is 0; t is 1; $Ar^1$ represents phen-1,4-ylene optionally substituted with one or two $R^5$ substituents; n is 2 and the —$CONR^7R^8$ group is in the para position; and $R^8$ is hydrogen.

8. The pharmaceutical composition of claim 7, wherein $R^5$ is independently selected from halo, (1-4C)alkyl, and (1-4C)alkoxy, wherein each alkyl and alkoxy group is optionally substituted with from 1 to 3 fluoro substituents.

9. The pharmaceutical composition of claim 1, wherein the compound is biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable salt thereof.

10. The pharmaceutical composition of claim 1, which is suitable for administration by inhalation.

11. The pharmaceutical composition of claim 10, which is in the form of an aerosol.

12. The pharmaceutical composition of claim 10, which is in the form of a powder.

13. The pharmaceutical composition of claim 10, which is in the form of a solution.

14. The pharmaceutical composition of claim 10, wherein the compound is micronized.

15. The pharmaceutical composition of claim 14, wherein the compound is combined with the carrier to form a suspension.

16. The pharmaceutical composition of claim 15, wherein the carrier is an isotonic aqueous solution.

17. The pharmaceutical composition of claim 14, wherein the compound is combined with the carrier to form a free flowing powder.

18. The pharmaceutical composition of claim 17, wherein the carrier is lactose or starch.

19. The pharmaceutical composition of claim 10, which further comprises a liquefied propellant.

20. The pharmaceutical composition of claim 10, which is administered using a nebulizer inhaler.

21. The pharmaceutical composition of claim 10, which is administered using a metered-dose inhaler.

22. The pharmaceutical composition of claim 10, which is administered using a dry powder inhaler.

* * * * *

UNITED STATES PATENT AND TRADEMARK OFFICE
CERTIFICATE OF CORRECTION

PATENT NO. : 7,550,595 B2
APPLICATION NO. : 11/880002
DATED : June 23, 2009
INVENTOR(S) : Mathai Mammen et al.

Page 1 of 1

It is certified that error appears in the above-identified patent and that said Letters Patent is hereby corrected as shown below:

Column 62
Lines 60-65, the structure should be

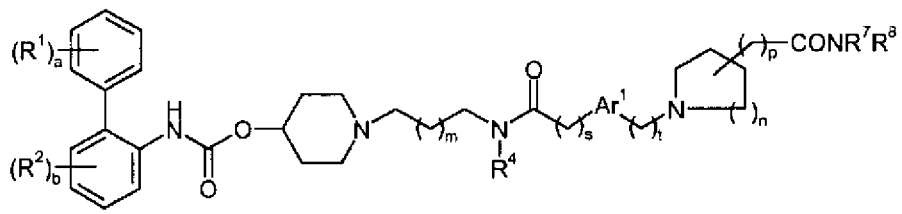

Signed and Sealed this

Twenty-fourth Day of November, 2009

David J. Kappos
*Director of the United States Patent and Trademark Office*